US008809804B2

(12) United States Patent
Mayfield et al.

(10) Patent No.: US 8,809,804 B2
(45) Date of Patent: Aug. 19, 2014

(54) HOLDER AND TOOL FOR RADIOISOTOPE ELUTION SYSTEM

(75) Inventors: Scott Hayward Mayfield, Florissant, MO (US); Kevin Robert Martz, Desoto, MO (US); Anthony K. Lewis, St. Charles, MO (US); Andrew D. Speth, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 13/353,923

(22) Filed: Jan. 19, 2012

(65) Prior Publication Data

US 2012/0305800 A1 Dec. 6, 2012

Related U.S. Application Data

(63) Continuation-in-part of application No. 29/383,507, filed on Jan. 19, 2011, now Pat. No. Des. 657,886.

(51) Int. Cl.
   *B01D 59/00* (2006.01)
   *G21F 5/015* (2006.01)
   *G21G 1/00* (2006.01)
   *G21F 5/06* (2006.01)

(52) U.S. Cl.
   CPC ............ *G21F 5/015* (2013.01); *G21G 1/0005* (2013.01); *G21F 5/06* (2013.01)
   USPC .................. 250/432 PD; 250/428; 250/432 R

(58) Field of Classification Search
   None
   See application file for complete search history.

(56) References Cited

U.S. PATENT DOCUMENTS

| 3,369,121 | A | * | 2/1968 | Bruno et al. ............... 250/432 R |
| 3,615,869 | A | * | 10/1971 | Barker et al. .............. 136/236.1 |
| 3,655,981 | A | * | 4/1972 | Montgomery et al. . 250/432 PD |
| 3,663,306 | A | | 5/1972 | Des Champs et al. |
| 3,673,411 | A | | 6/1972 | Glasser |
| 3,710,118 | A | * | 1/1973 | Holgate et al. ............ 250/432 R |

(Continued)

FOREIGN PATENT DOCUMENTS

| EP | 739017 A1 * | 10/1996 | ................ G21F 1/12 |
| GB | 1473236 | 5/1977 | |

(Continued)

OTHER PUBLICATIONS

International Search Report and Written Opinion of the International Searching Authority regarding PCT/US2013/021860 mailed on Dec. 3, 2013, 16 pgs.

(Continued)

*Primary Examiner* — Andrew Smyth
(74) *Attorney, Agent, or Firm* — Armstrong Teasdale LLP

(57) ABSTRACT

A holder for a vial containing a sterile liquid for use with a radiopharmaceutical elution system includes a holder body. The body has a top, an opposing bottom, an opening in the top and a vial chamber. The vial chamber extends from the opening in the top toward the bottom and is sized and shaped for receiving the vial therein. An access opening extends through the bottom to the vial chamber and is aligned with a septum of the elution vial when the sterile vial is received in the vial chamber. A cap is removably secured to the top of the holder body for selectively opening and closing the vial chamber. The holder body includes plastic and has a density less than the density of the cap.

13 Claims, 40 Drawing Sheets

(56) References Cited

U.S. PATENT DOCUMENTS

| | | | |
|---|---|---|---|
| 3,920,995 A * | 11/1975 | Czaplinski et al. | 250/432 R |
| D239,120 S | 3/1976 | Heyer | |
| 3,946,238 A * | 3/1976 | Fries | 250/432 PD |
| 4,020,351 A * | 4/1977 | Gemmill et al. | 250/432 PD |
| 4,084,097 A * | 4/1978 | Czaplinski et al. | 250/506.1 |
| 4,160,910 A * | 7/1979 | Thornton et al. | 250/432 PD |
| 4,188,539 A * | 2/1980 | Strecker | 250/432 PD |
| 4,241,728 A | 12/1980 | Mirell | |
| 4,245,685 A * | 1/1981 | Nemitz et al. | 220/780 |
| 4,308,460 A | 12/1981 | Groh et al. | |
| 4,387,303 A * | 6/1983 | Benjamins | 250/432 PD |
| 4,395,159 A | 7/1983 | Karuks et al. | |
| 4,663,115 A * | 5/1987 | Russell | 376/320 |
| 4,782,231 A * | 11/1988 | Svoboda et al. | 423/249 |
| 4,846,235 A | 7/1989 | Handke | |
| 5,109,160 A | 4/1992 | Evers | |
| 5,109,196 A | 4/1992 | Wikswo, Jr. et al. | |
| 5,111,099 A * | 5/1992 | Smith | 310/305 |
| 5,199,597 A | 4/1993 | Gladish | |
| 5,225,165 A | 7/1993 | Perlman | |
| 5,274,239 A | 12/1993 | Lane et al. | |
| 5,309,959 A * | 5/1994 | Shaw et al. | 141/130 |
| 5,382,408 A | 1/1995 | Perlman | |
| 5,397,902 A | 3/1995 | Castner et al. | |
| 5,479,969 A * | 1/1996 | Hardie et al. | 141/130 |
| 5,552,612 A | 9/1996 | Katayama et al. | |
| 5,582,315 A * | 12/1996 | Reid | 220/254.4 |
| D389,761 S | 1/1998 | Thomas | |
| 5,734,169 A | 3/1998 | Saidian | |
| 5,795,061 A | 8/1998 | Perlman | |
| 5,834,788 A | 11/1998 | Fu et al. | |
| 6,096,561 A | 8/2000 | Tayi | |
| 6,190,617 B1 | 2/2001 | Clark et al. | |
| 6,238,374 B1 * | 5/2001 | Winkler | 604/256 |
| D506,261 S | 6/2005 | Hellstrom | |
| 7,060,998 B2 * | 6/2006 | Forrest et al. | 250/506.1 |
| 7,091,494 B2 * | 8/2006 | Weisner et al. | 250/432 PD |
| 7,241,482 B2 | 7/2007 | Ferrand | |
| D589,157 S | 3/2009 | Speth | |
| 7,504,646 B2 * | 3/2009 | Balestracci et al. | 250/507.1 |
| 7,592,605 B2 * | 9/2009 | Weisner et al. | 250/432 PD |
| D602,164 S | 10/2009 | Speth et al. | |
| D607,117 S * | 12/2009 | Horton et al. | D24/224 |
| 7,700,926 B2 | 4/2010 | Tartaglia et al. | |
| D617,910 S | 6/2010 | Horton et al. | |
| 7,753,835 B2 * | 7/2010 | Van Der Lee et al. | 600/3 |
| 7,772,565 B2 * | 8/2010 | Wilson | 250/428 |
| 7,812,322 B2 * | 10/2010 | Wagner et al. | 250/432 R |
| 7,838,844 B2 * | 11/2010 | Wagner et al. | 250/432 PD |
| D634,184 S | 3/2011 | Koehn | |
| D644,323 S | 8/2011 | Burgess et al. | |
| 8,003,967 B2 * | 8/2011 | Fago et al. | 250/506.1 |
| 8,044,377 B2 | 10/2011 | Helle et al. | |
| 8,231,858 B2 * | 7/2012 | Storey et al. | 424/1.11 |
| 2005/0104016 A1 * | 5/2005 | Forrest et al. | 250/506.1 |
| 2005/0116186 A1 * | 6/2005 | Weisner et al. | 250/505.1 |
| 2005/0253085 A1 * | 11/2005 | Weisner et al. | 250/432 PD |
| 2007/0071670 A1 * | 3/2007 | Storey et al. | 424/1.11 |
| 2008/0167621 A1 * | 7/2008 | Wagner et al. | 604/191 |
| 2008/0185532 A1 * | 8/2008 | Wilson | 250/428 |
| 2008/0191148 A1 * | 8/2008 | Gibson | 250/432 PD |
| 2008/0197302 A1 * | 8/2008 | Fago et al. | 250/506.1 |
| 2008/0200747 A1 * | 8/2008 | Wagner et al. | 600/5 |
| 2008/0203318 A1 * | 8/2008 | Wagner et al. | 250/432 PD |
| 2008/0210891 A1 * | 9/2008 | Wagner et al. | 250/507.1 |
| 2008/0224065 A1 * | 9/2008 | Pollard, Jr. | 250/432 R |
| 2008/0245977 A1 * | 10/2008 | Fago et al. | 250/505.1 |
| 2008/0277594 A1 * | 11/2008 | Wagner et al. | 250/432 PD |
| 2009/0266998 A1 * | 10/2009 | Horton et al. | 250/432 PD |
| 2011/0008222 A1 | 1/2011 | Bushman et al. | |
| 2011/0124948 A1 | 5/2011 | Yokell | |
| 2012/0305429 A1 | 12/2012 | Mayfield et al. | |
| 2013/0029073 A1 | 1/2013 | Mayfield et al. | |

FOREIGN PATENT DOCUMENTS

| | | | | |
|---|---|---|---|---|
| GB | 1532225 A | | 11/1978 | |
| GB | 2386743 A | * | 9/2003 | G21G 4/08 |
| JP | S54158199 U | | 11/1979 | |
| WO | WO 2007016172 A2 | * | 2/2007 | G21G 4/00 |

OTHER PUBLICATIONS

International Search Report and Written Opinion of the International Searching Authority regarding PCT/US2013/060869 mailed on Jan. 21, 2014, 11 pgs.

* cited by examiner

HOLDER AND TOOL FOR RADIOISOTOPE ELUTION SYSTEM

CROSS-REFERENCE TO RELATED APPLICATION

The present application is a continuation-in-part of U.S. patent application Ser. No. 29/383,507 filed Jan. 19, 2011, and having the title "Radiation Shielding Container Lid."

BACKGROUND

The present disclosure relates generally to a radioisotope elution system and tools for use therewith.

Nuclear medicine uses radioactive material for diagnostic and therapeutic purposes by injecting a patient with a dose of the radioactive material, which concentrates in certain organs or biological regions of the patient. Radioactive materials typically used for nuclear medicine include Technetium-99m, Indium-111, and Thallium-201 among others. Some chemical forms of radioactive materials naturally concentrate in a particular tissue, for example, radioiodine (I-131) concentrates in the thyroid. Radioactive materials are often combined with a tagging or organ-seeking agent, which targets the radioactive material for the desired organ or biologic region of the patient. These radioactive materials alone or in combination with a tagging agent are typically referred to as radiopharmaceuticals in the field of nuclear medicine. At relatively low doses of radiation from a radiopharmaceutical, a radiation imaging system (e.g., a gamma camera) may be utilized to provide an image of the organ or biological region in which the radiopharmaceutical localizes. Irregularities in the image are often indicative of a pathology, such as cancer. Higher doses of a radiopharmaceutical may be used to deliver a therapeutic dose of radiation directly to the pathologic tissue, such as cancer cells.

A variety of systems are used to generate, enclose, transport, dispense, and administer radiopharmaceuticals. One such system includes a radiopharmaceutical generator, including an elution column, and an input connector (e.g., an input needle) and an output connector (e.g., an output needle) in fluid communication with the elution column. Typically, a radiopharmacist or technician fluidly connects an eluant vial (e.g., a vial containing saline) to the input connector and fluidly connects an empty elution vial (e.g., a vial having at least a partial internal vacuum) to the output connector. The vacuum in the empty elution vial draws the eluant (e.g., saline) from the eluant vial through the elution column, and into the elution vial. The saline elutes radioisotopes as its flows through the elution column so that radioisotope-containing saline fills the elution vial. The elution vial is typically housed in its own radiation shielding container, sometimes referred to as pharmacy shield or an elution shield.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

In one aspect, a holder for a vial containing a sterile liquid for use with a radiopharmaceutical elution system includes a holder body. The body has a top, an opposing bottom, an opening in the top and a vial chamber. The vial chamber extends from the opening in the top toward the bottom and is sized and shaped for receiving the vial therein. An access opening extends through the bottom to the vial chamber and is aligned with a septum of the elution vial when the sterile vial is received in the vial chamber. A cap is removably secured to the top of the holder body for selectively opening and closing the vial chamber. The cap includes at least one of depleted uranium, tungsten, tungsten impregnated plastic. The holder body includes plastic and has a density less than the density of the cap.

In another aspect, a radiation shield for an eluant vial includes a shield body having a closed top and an open bottom. A cavity extends from the bottom toward the top and is designed to accommodate at least a bottom portion of an eluant vial. A pair of shielding wings extends downward from the bottom and partially surrounds the cavity. The shield body and the shielding wings include at least one of depleted uranium, tungsten, tungsten impregnated plastic.

Yet another aspect is directed to a re-covering tool for re-covering inlet and outlet needles of a radiopharmaceutical generator. The re-covering tool includes a first longitudinal portion having a first outer diameter and defining a first cavity in which an outlet needle cover for the outlet needle is disposed. The tool also includes a second longitudinal portion having a second outer diameter and defining a second cavity in which an inlet needle cover for the inlet needle is disposed. The first outer diameter is greater than the second outer diameter.

Various refinements exist of the features noted in relation to the above-mentioned aspects of the present disclosure. Further features may be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

DETAILED DESCRIPTION OF THE ILLUSTRATED EMBODIMENTS

Figure 1A:
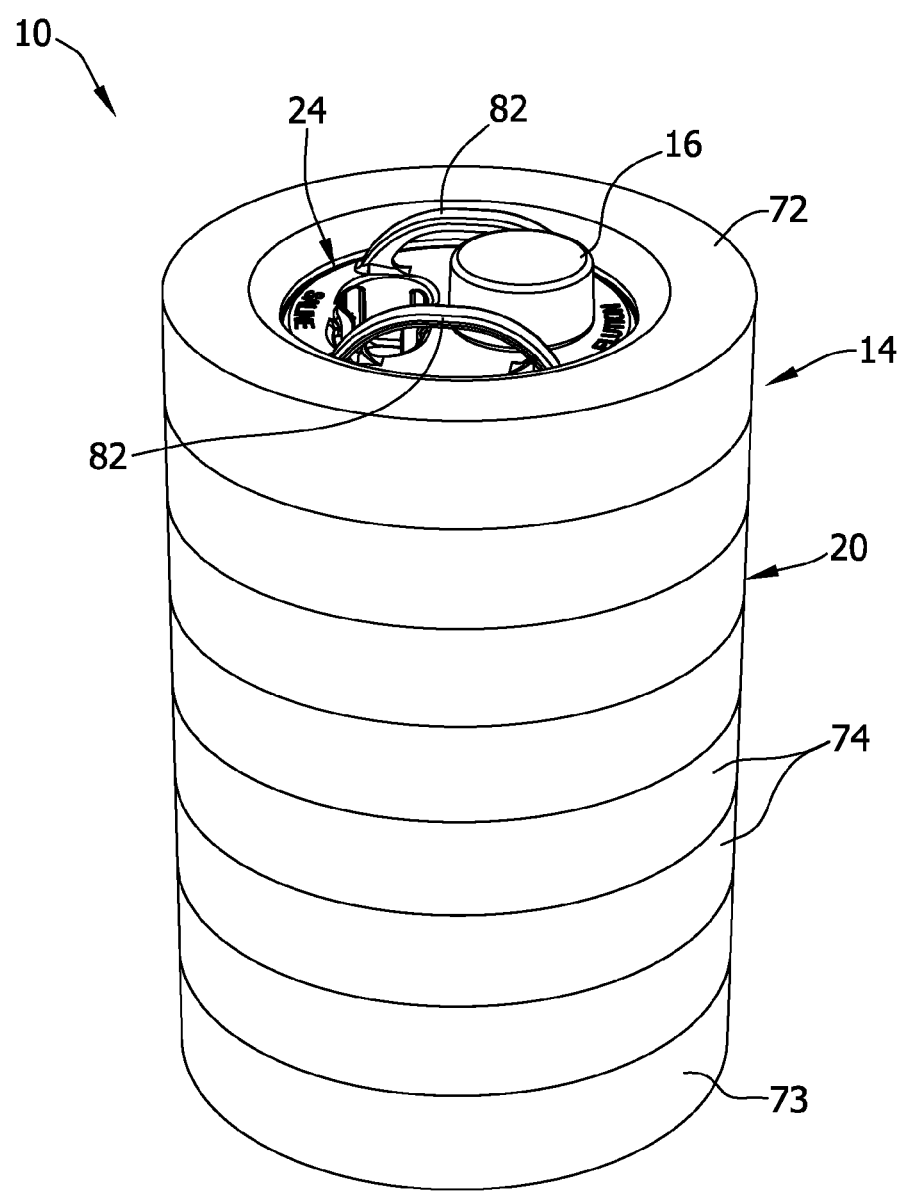
FIGS. 1A and 1B are perspectives of one embodiment of a radioisotope elution system.
Figure 1B:
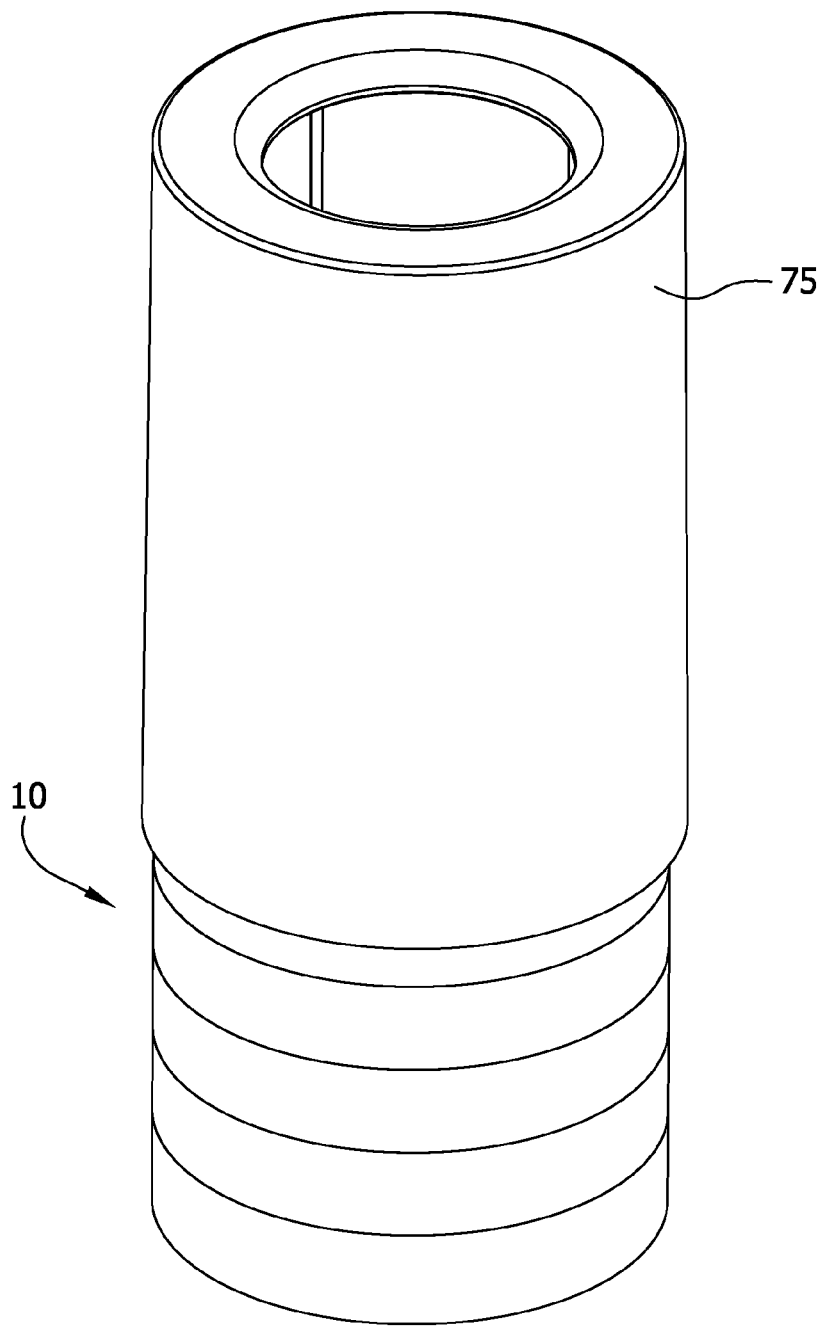
Figure 2:
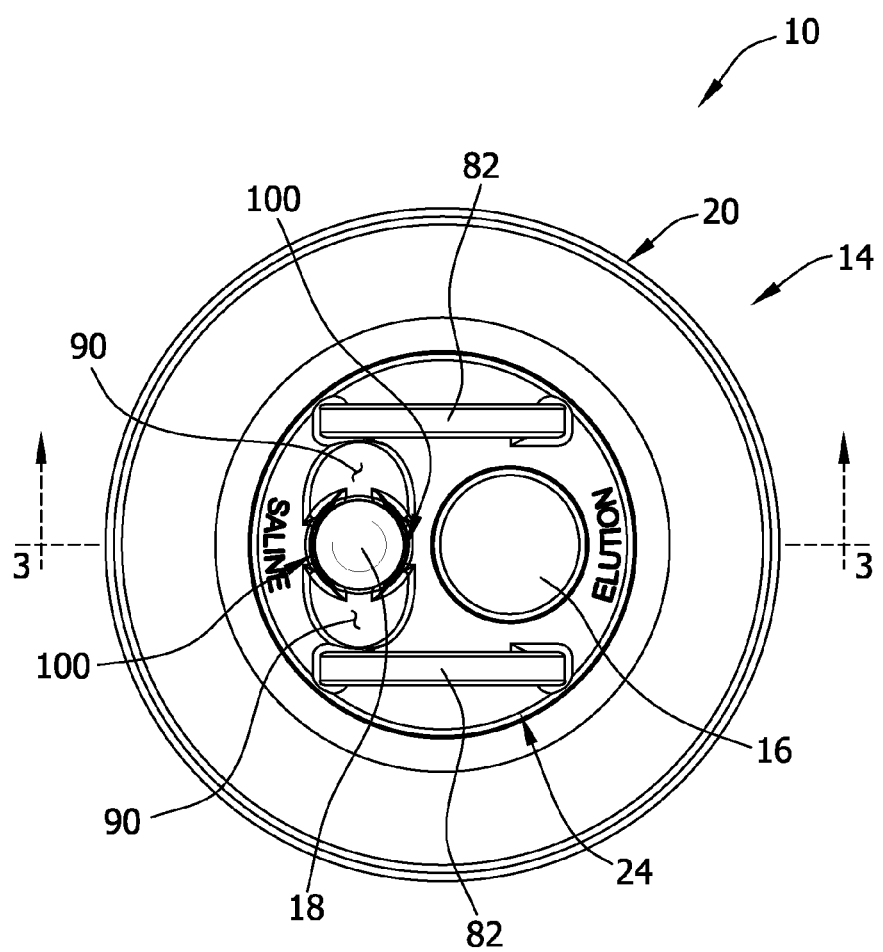
FIG. 2 is a top plan view of the radioisotope elution system of FIG. 1.

Referring to FIGS. 1A-4, one embodiment of a radioisotope elution system 10 includes a radioisotope generator 12 (FIGS. 3 and 4), which is removably receivable in an auxiliary shield assembly 14. As explained in more detail below, an elution tool 16, which houses an elution vial 17 (broadly, a container), and an eluant vial 18 (broadly, a container) are fluidly connectable to the radioisotope generator 12. Herein, "fluidly connectable" refers to the ability of first component and a second component to be connected (either directly or indirectly) or interface in a manner such that fluid (e.g., eluate, eluant) may flow therebetween in a substantially confined flow path. The auxiliary shield assembly 14 includes a radiation shielding body 20 that defines a cavity 22 in which the generator 12 is removably receivable, and a radiation shielding lid 24 that may be positioned on the body 20 toward a top thereof to substantially enclose the cavity 22 defined in the body 20. In general, the radiation shielding lid 24 facilitates proper alignment of the eluant vial 18 with the radioisotope generator 12 when fluidly connecting the eluant vial with the radioisotope generator. Additional disclosure of the radiation shielding lid 24 is set forth in detail below.

The elution tool 16 illustrated in FIGS. 1-11 may be of any appropriate configuration (e.g., size, shape, design), as is known to one having ordinary skill in the art, and may include one or more suitable radiation shielding materials, such as depleted uranium, tungsten, tungsten impregnated plastic, or lead. A second embodiment of the elution tool is illustrated in FIGS. 22-33 and described in detail below. The illustrated elution vial 17 is a generally cylindrical container, made from glass or other material (e.g., plastic), which includes a septum 17a secured to a top portion thereof by a metal ring or cap 17b, as is generally known in the art. The elution vial 17 may be a different type of container suitably connectable to a radioisotope generator and/or may have a shape other than generally cylindrical. In one embodiment, the interior of the elution vial 17 is at least partially evacuated such that the elution vial has a reduced internal pressure (i.e., at least a partial vacuum). The eluant vial 18, like the elution vial 17, may be a generally cylindrical container, which includes a septum (not shown) secured to a top portion thereof by a metal ring or cap (not shown), as is generally known in the art. The eluant vial 18 may be a different type of container suitably connectable to a radioisotope generator and/or may have a shape other than generally cylindrical. The eluant vial 18 is filled with an eluant fluid, such as saline. In one embodiment, the volume of eluant fluid is less than the volume of the elution vial 17. In another embodiment, the interior volume of eluant vial 18 is less than the interior volume of the elution vial 17. For example, the eluant vial 18 may have an internal volume of about 26 milliliters, and the interior volume of the elution vial 17 may be about 36 milliliters. The elution vial 17 and/or the eluant vial 18 may be of other configurations without departing from the scope of the present disclosure.

Figure 3:
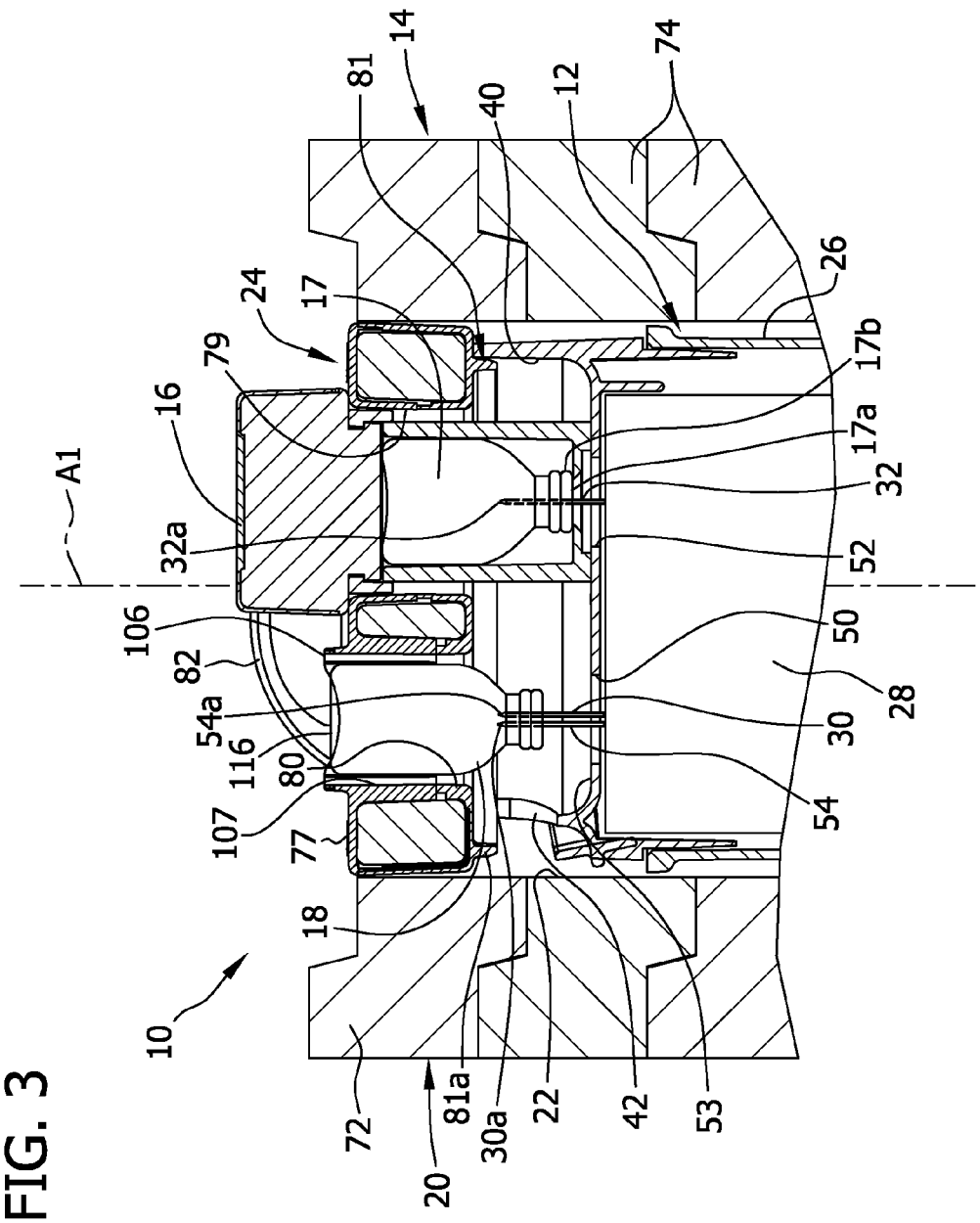
FIG. 3 is a cross section of the radioisotope elution system of FIG. 1 taken along line 3-3 in FIG. 2.
Figure 4:
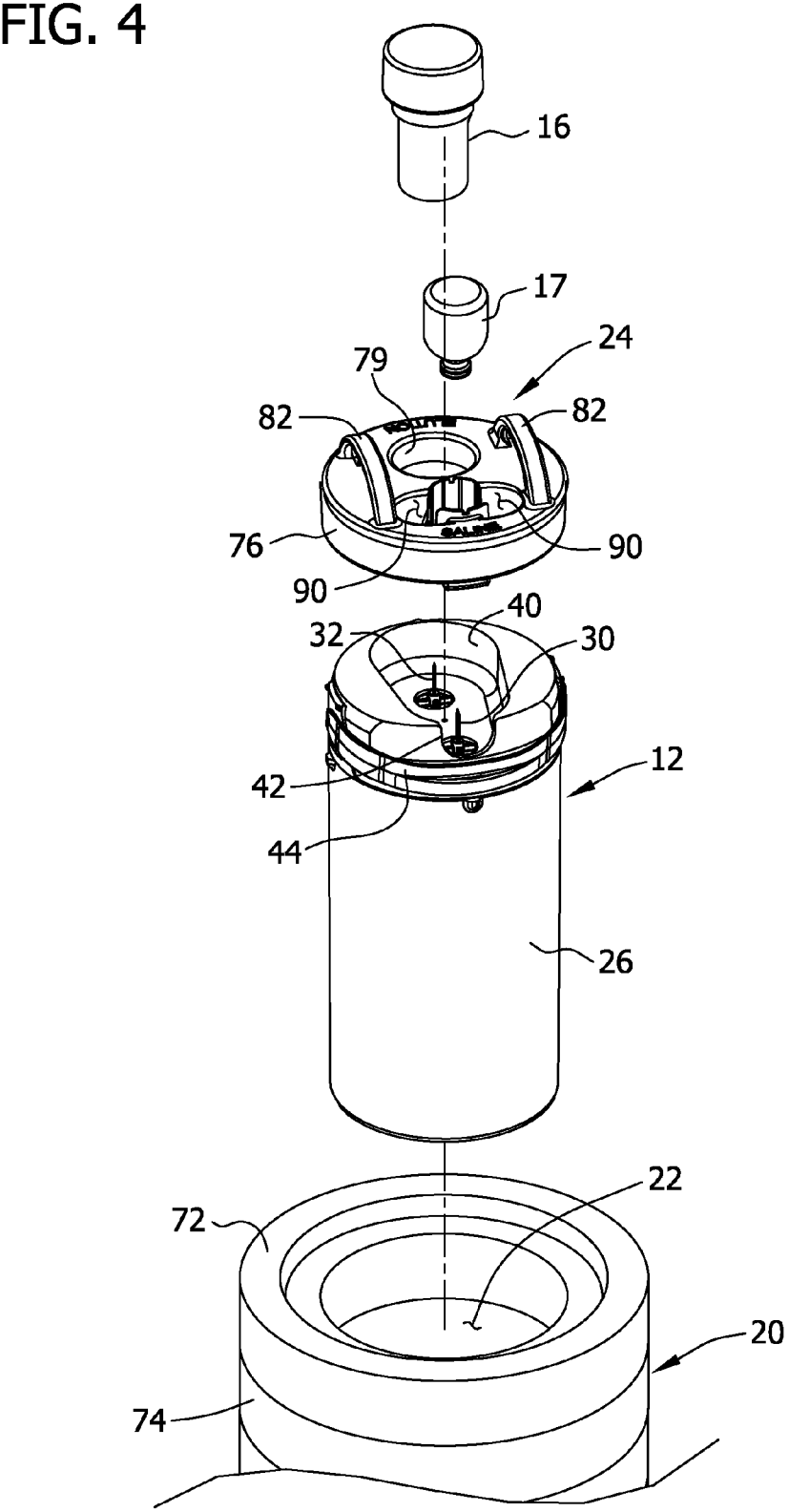
FIG. 4 is an exploded view of the radioisotope elution system of FIG. 1.
Figure 5:
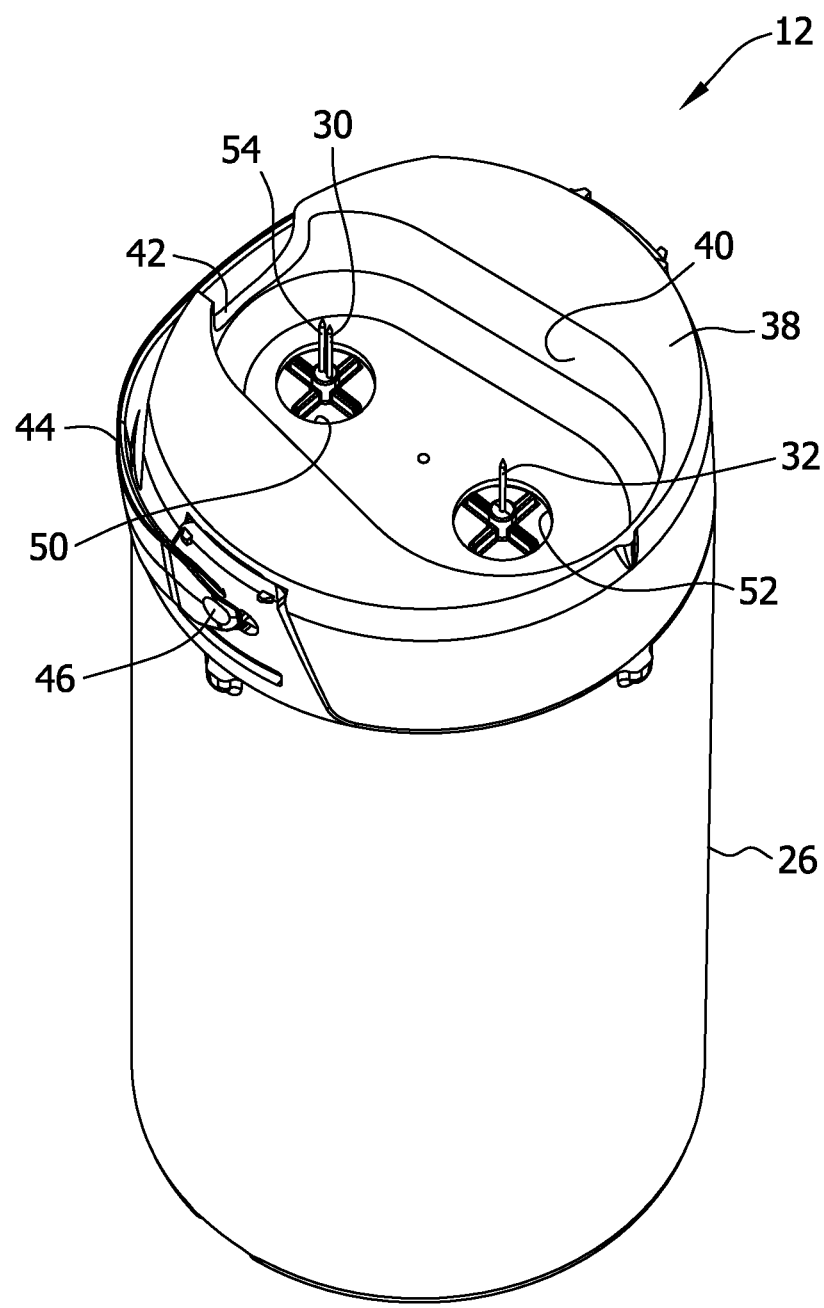
FIG. 5 is an enlarged perspective of a radioisotope generator of the radioisotope elution system of FIG. 1.
Figure 6:
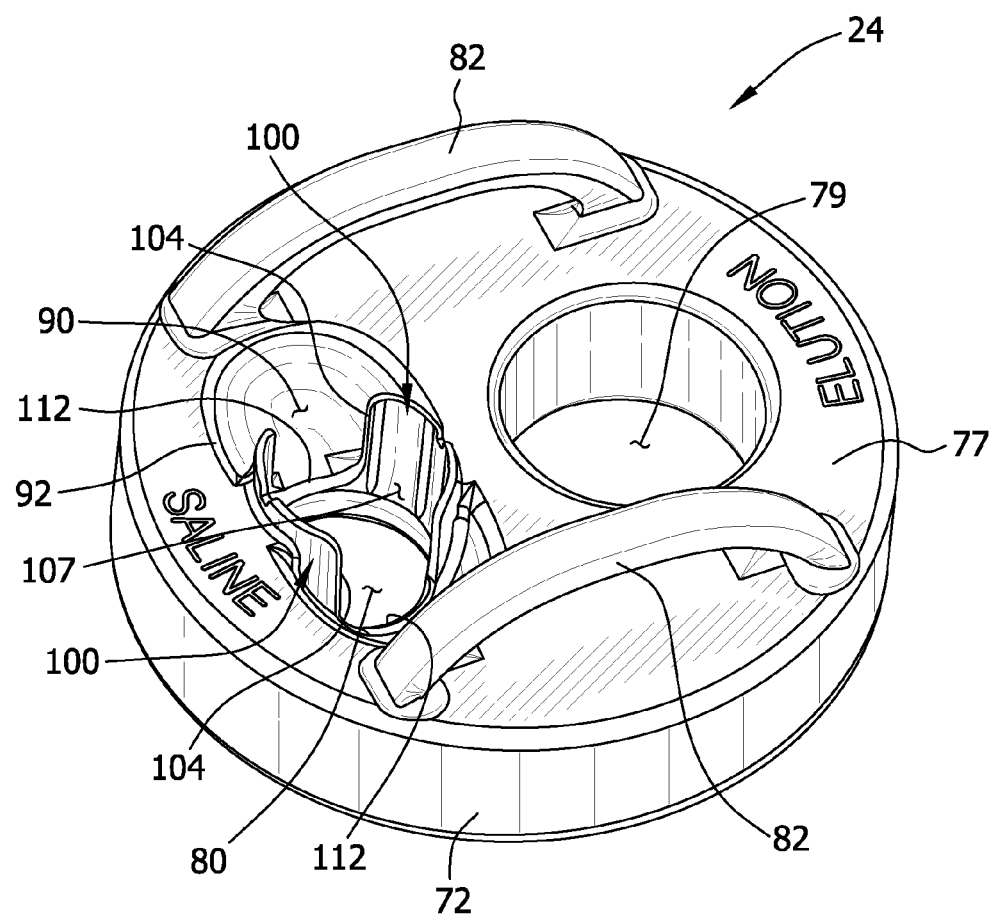
FIG. 6 is an enlarged perspective of an auxiliary shield assembly lid of the radioisotope elution system of FIG. 1.
Figure 7:
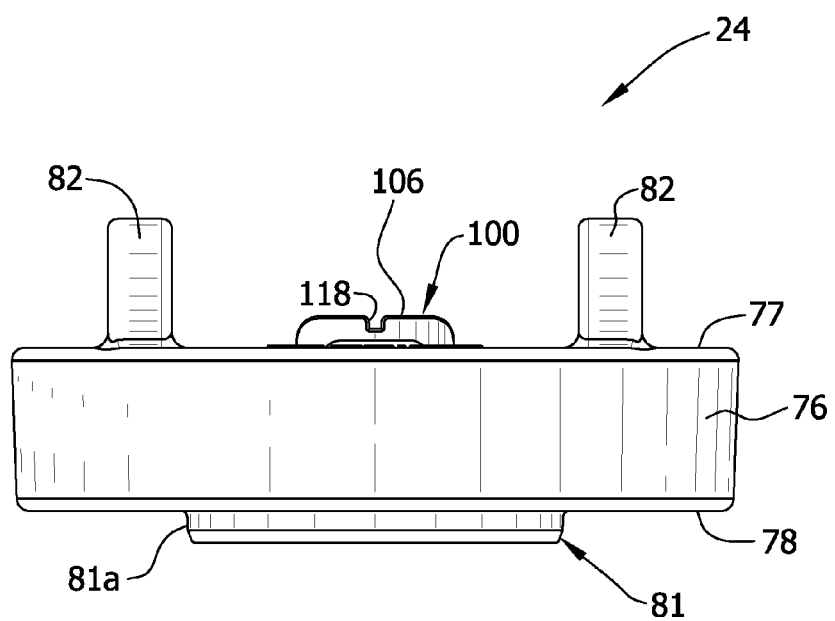
FIG. 7 is a front elevation of the auxiliary shield assembly lid of FIG. 6.

Referring to FIGS. 3-5, the radioisotope generator 12 includes: a housing 26; an elution column assembly 28 (FIG. 3) disposed within the housing; and input and output connectors 30, 32, respectively, in fluid communication with the elution column assembly 28; and a hood or cap 38 secured to the housing. The generator housing 26 is generally cylindrical and defines an axially extending cavity in which the elution column assembly 28 is received. The housing cap 38 may be snap-fit on the housing 26, or secured thereto in any other appropriate manner. The housing cap 38 has a recessed portion 40 extending downward from an upper surface of the cap. The cap 38 also has a generally U-shaped channel 42 extending downward from the upper surface and through a sidewall of the cap to the recessed portion 40. As explained in more detail below, the recessed portion 40 and the channel 42 together constitute an alignment structure, more specifically female alignment structure, for facilitating proper alignment of the radiation shielding lid 24 on the generator 12. The generator housing 26 and cap 38 may be formed from plastic (such as by molding) or from other suitable, preferably lightweight, material. Moreover, the generator housing 26 itself may be free from lead, tungsten, tungsten impregnated plastic, depleted uranium, or other radiation shielding material, such that the housing provides little or only nominal radiation shielding.

The generator 12 includes a generator handle 44 pivotally secured to the cap 38. The handle 44 is pivotable between a stored position, in which the handle lies in a plane substantially transverse to the axis A1 of the housing 26 (FIG. 3) and below the upper surface of the cap 38, and a carrying position, in which the handle lies in a plane substantially parallel to the axis of the housing and above the upper surface of the cap. The generator handle 44 allows a radiopharmacist or technician to lift the generator 12 for placement of the generator in the auxiliary shield assembly 14 and removal of the generator from the auxiliary shield assembly. The generator handle 44 may be formed from plastic or any other appropriate material and may be pivotally connected to the generator housing 26 by pivot connectors 46 (FIG. 5) or in any other appropriate manner of connection.

Referring to FIG. 3, the input and output connectors 30, 32 extend upward from the elution column assembly 28 and through respective input opening 50 and output opening 52 in a bottom surface 53 of the recessed portion 40 of the generator cap 38 such that respective terminal ends or tips 30a, 32a of the input and output connectors are disposed within the recessed portion. In the illustrated embodiment, the input and output connectors 30, 32 respectively include input and output needles or needles 30, 32 for piercing respective septums 17a of the elution vial 17 and the eluant vial 18, although it is contemplated that the connectors may be of other configurations/types. In addition to the input and output connectors 30, 32, a venting needle 54, in fluid communication with atmosphere, extends through the bottom surface 53 of the recessed portion 40 of the cap 38. The venting needle 54 is adjacent to the input connector 30 and extends through the same input opening 50 in the generator cap 38. In the illustrated embodiment, the venting needle 54 includes a needle having a terminal end or tip 54a disposed within the recessed portion 40 of the generator cap 38. The venting needle 54 pierces the septum 17a of the eluant vial 18, like the input needle 30, to vent the eluant vial 18 to atmosphere.

Figure 12:
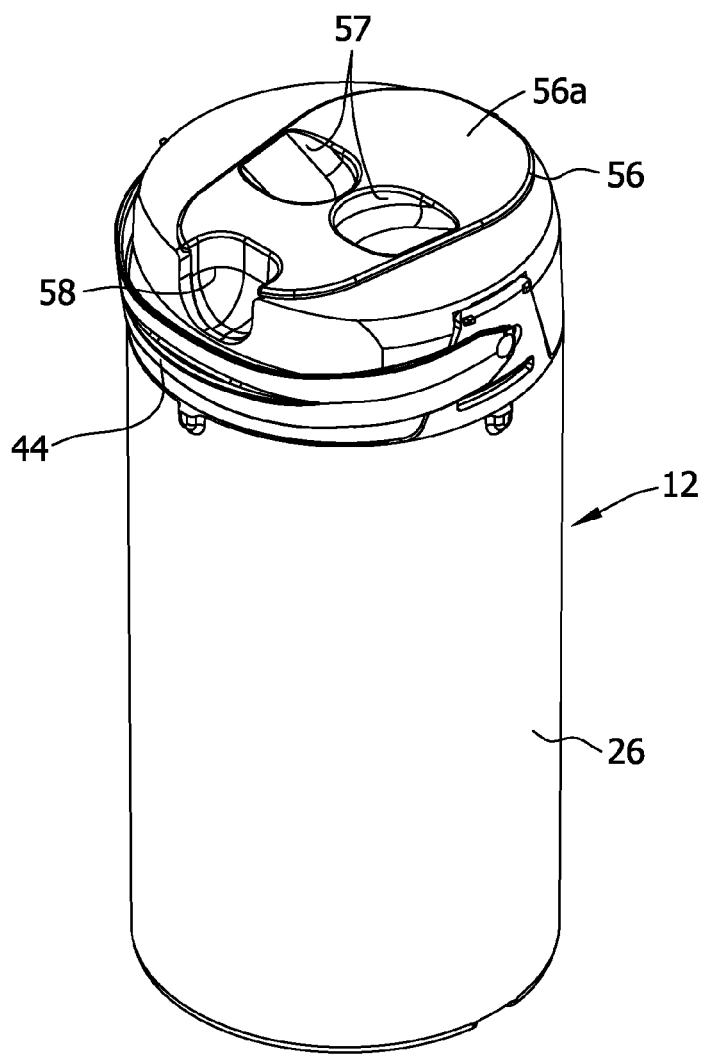
FIG. 12 is a perspective of the radioisotope generator in a non-use configuration including a cap cover.
Figure 13:
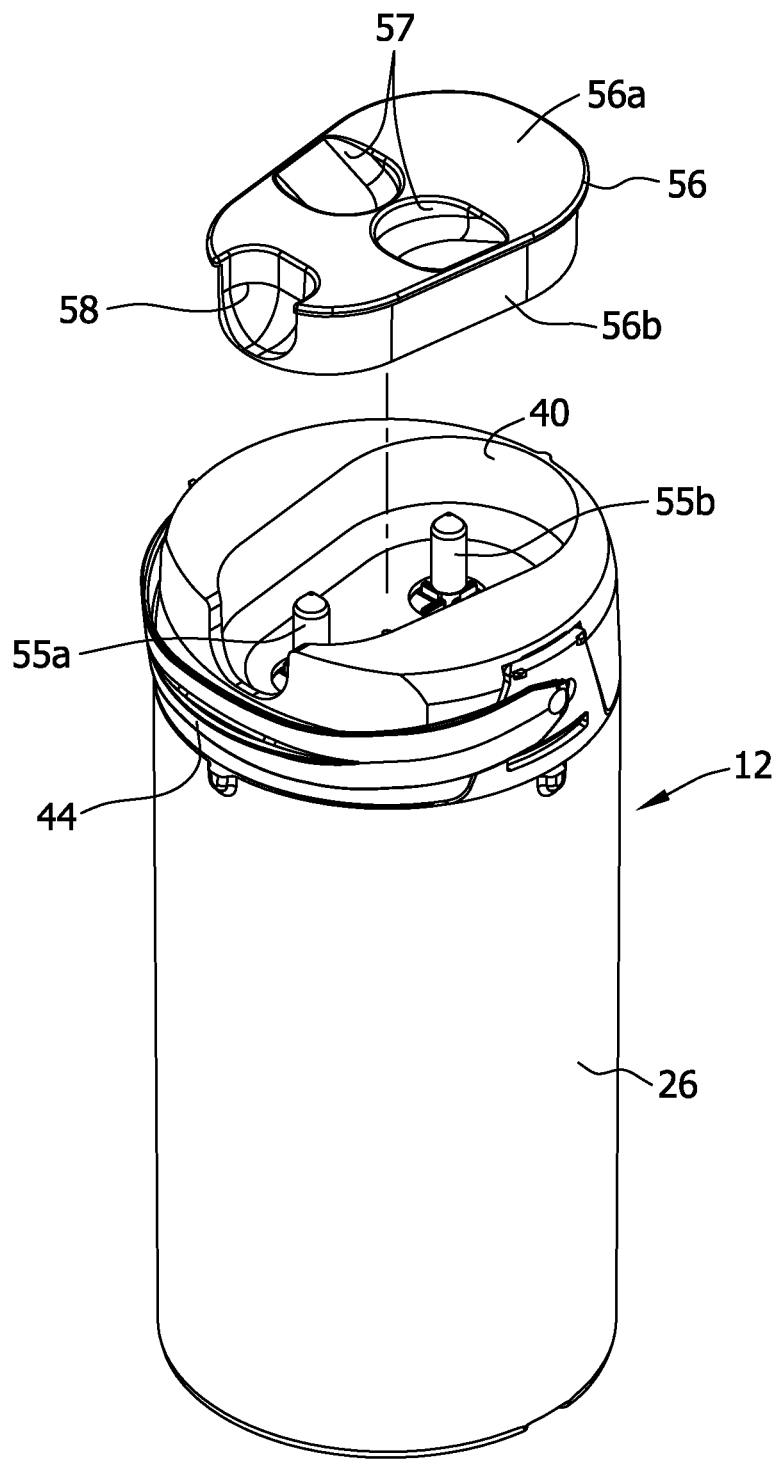
FIG. 13 is similar to FIG. 12, but with the cap cover removed from the cap of the radioisotope generator.

As shown in FIGS. 12-13, in a non-use configuration of the generator—such as during shipping—the generator 12 may include needle covers 55a, 55b and a cap cover 56. In the illustrated embodiment, the needle covers include an input/venting needle cover 55a removably secured directly to the input needle 30 and the venting needle 54, and an output needle cover 55b removably secured directly to the output needle 32. The needle covers 55a, 55b protect the respective needles 30, 32, 54 and inhibit contaminants from entering the elution column assembly 28 via the needles. The illustrated needle covers 55a, 55b are solid, non-hollow, one-piece members made of a suitable material (e.g., silicone) that is pierceable by the needles 30, 32, 54. Before operating the elution system 10, a technician can remove the needle covers 55a, 55b using forceps or another suitable instrument. It is understood that the elution system 10 may not include the needles covers 55a, 55b, or the needle covers may be of other configurations without departing from the scope of the present invention.

Referring still to FIGS. 12-13, the cap cover 56 is removably insertable in the recessed portion 40 of the generator cap 38 to cover and protect the input, output, and venting needles 30, 32, 54, respectively. The cap cover 56 has a top surface 56a that is disposed over and covers the needles 30, 32, 54 when the cap cover is secured to the generator 12, and a sidewall 56b depending downward from the top surface that frictionally engages the sidewall of the recessed portion 40 such that the cap cover is removably retained in the recessed portion by friction-fit connection. The cap cover 56 has two finger recesses 57 in the top surface 56a thereof, and a thumb recess 58 in the top surface and the sidewall 56b thereof. A technician can grip and remove the cap cover 56 using a single hand by inserting one or more of his/her fingers into each of the finger recesses 57 and inserting his/her thumb into the thumb recess 58, and then lifting the cap cover upward and out of the recessed portion 40. It is understood that a cap cover have other configurations and/or can be removably secured to the generator 12 in other ways without departing from the scope of the present invention. It is also understood that the elution system 10 may not include a cap cover without departing from the scope of the present invention.

Figure 14:
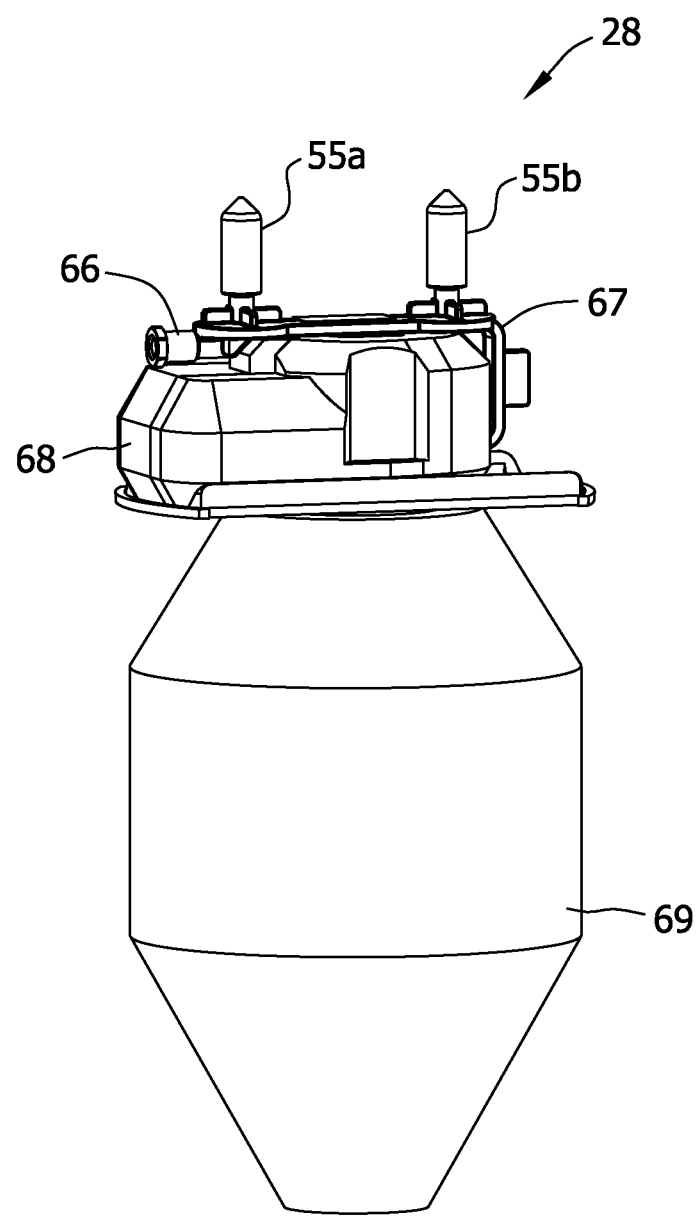
FIG. 14 is a perspective of the elution column assembly removed from a housing of the radioisotope generator.
Figure 15:
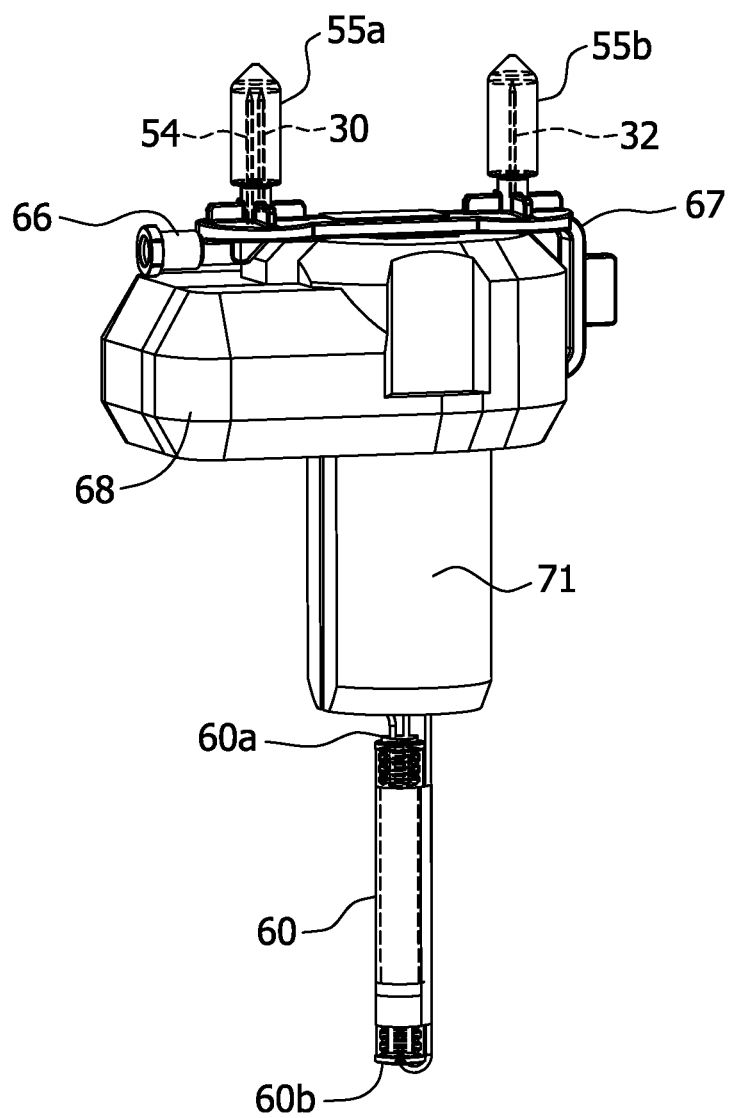
FIG. 15 is similar to FIG. 14, but with a column shield of the elution column assembly removed therefrom.
Figure 16:
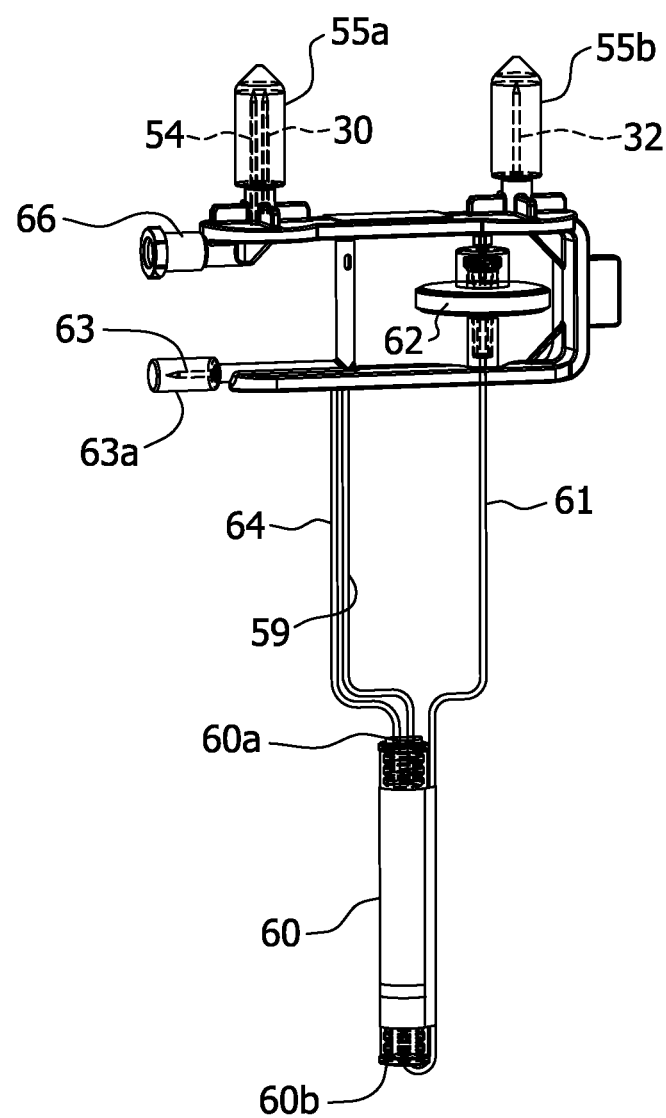
FIG. 16 is similar to FIG. 15, but with a conduit shield of the elution column assembly removed therefrom.
Figure 17:
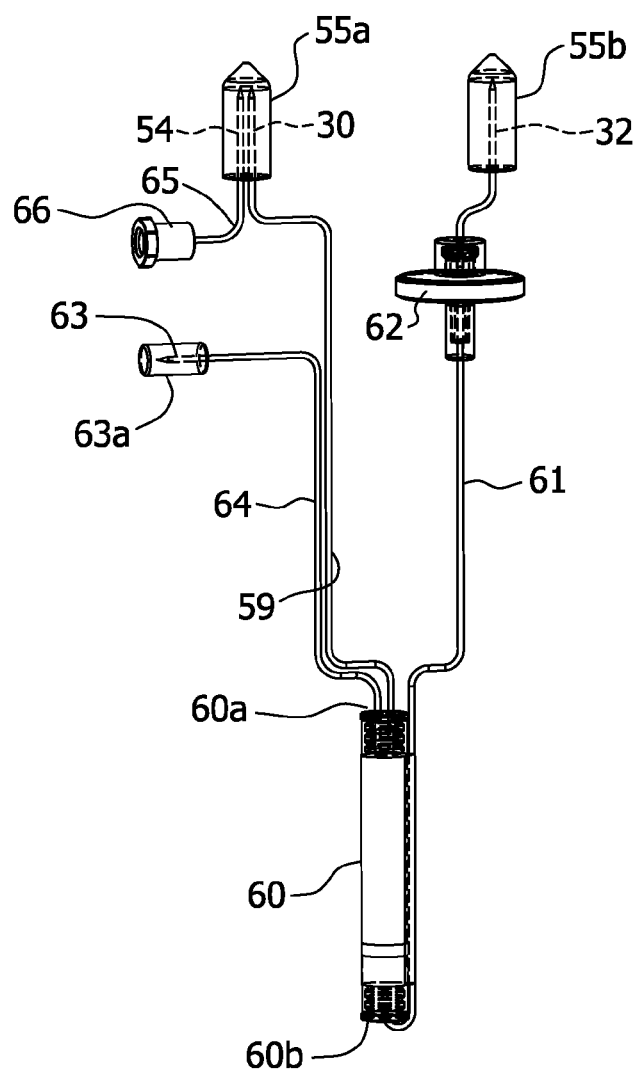
FIG. 17 is similar to FIG. 16, but with a U-shaped support of the elution column assembly removed therefrom.
Figure 18:
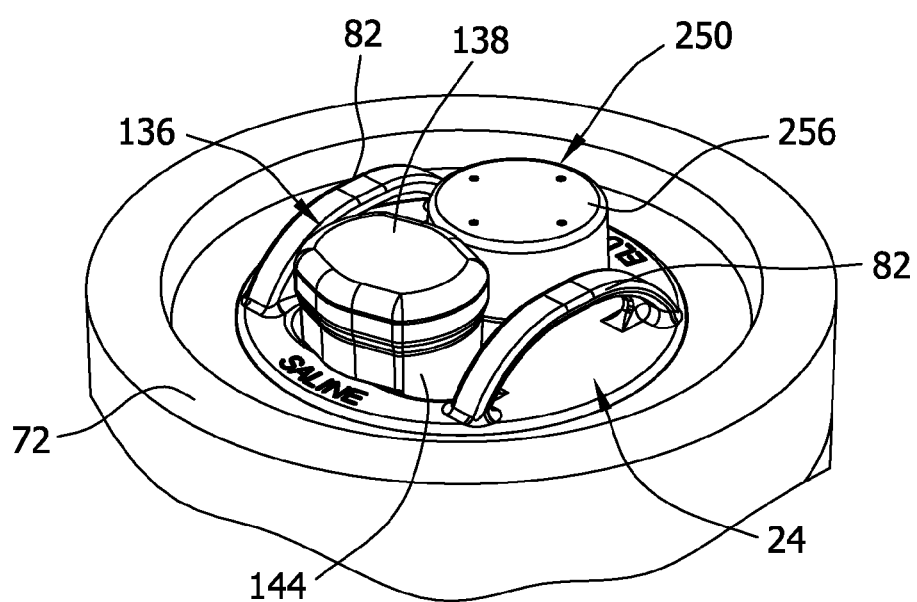
FIG. 18 is a partial perspective of the elution system, including an eluant shield and a sterile vial holder on the lid of the auxiliary shield.
Figure 19:
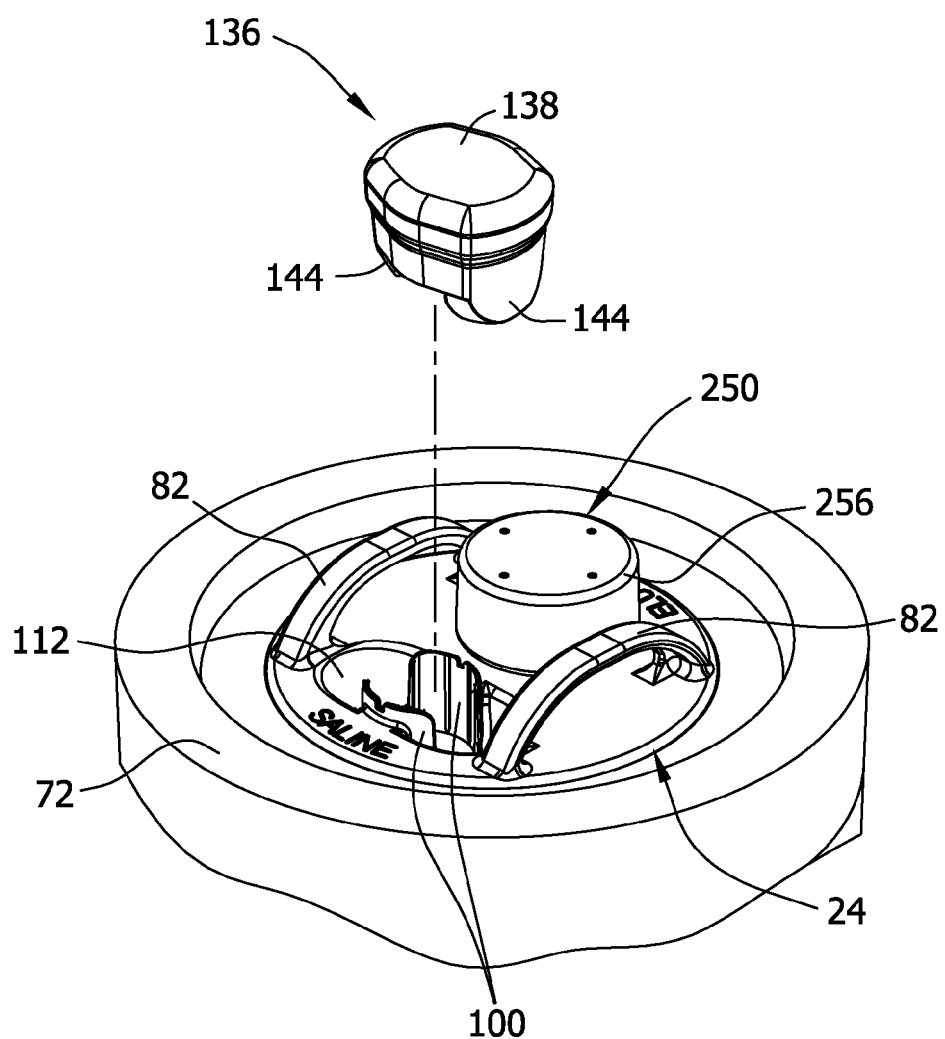
FIG. 19 is similar to FIG. 18, but with the eluant shield removed therefrom.
Figure 20:
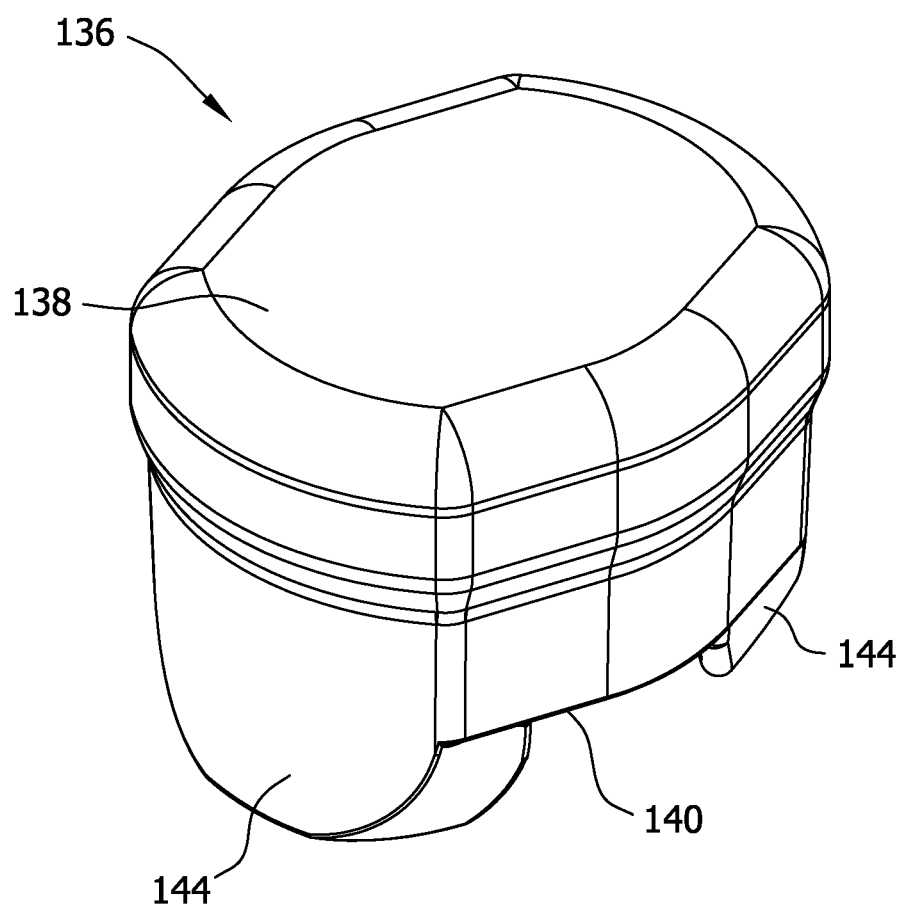
FIG. 20 is an enlarged top perspective of the eluant shield.
Figure 21:
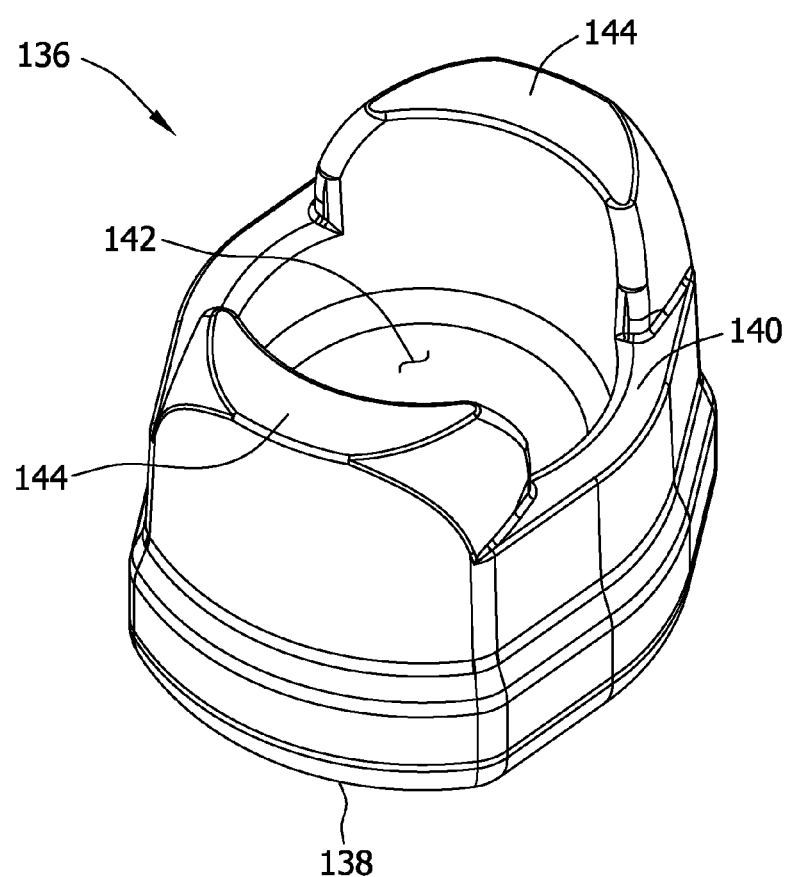
FIG. 21 is an enlarged bottom perspective of the eluant shield.

Referring to FIGS. 14-17, one embodiment of the elution column assembly 28 is shown in detail. As shown in FIGS. 16 and 17, an input conduit 59 extends from the input connector 30 and into a top 60a of an elution column 60 to fluidly connect the input connector to the elution column. An output conduit 61 extends from a bottom 60b of the elution column 60 to the output connector 32 to fluidly connect the elution column to the output connector. The input and output conduits 59, 61, respectively, can be made from suitable material, such as Inconel 625. The elution column 60 may include a source of radioactive material therein (e.g., molybdenum-99, adsorbed to the surfaces of beads of alumina or a resin exchange column). In the illustrated embodiment, a filter 62 (e.g., a conventional 0.2 micron filter) is fluidly connected to, and inline with, the output conduit 61. A fillport needle 63 is fluidly connected to conduit 64, which is in turn fluidly connected to the elution column 60 for loading the product (fillport needle is typically only accessed during loading and not accessed by the technician). A cover 63a, similar to the needle covers 55a, 55b, described above, is removably attached to the needle 63. A venting conduit 65 (FIG. 17) fluidly connects the venting needle 54 with the atmosphere. The venting conduit 65 has a terminal end on which an air filter 66 is secured.

As shown in FIGS. 14-16, a generally rigid U-shaped support 67, which may be formed from plastic or other suitable, generally rigid material, provides structural support to the input and output needles 30, 32, the venting needle 54, and the fillport needle 63, and portions of the respective conduits 59, 61, 64, 65. As shown in FIGS. 14 and 15, the elution column assembly 28 also includes a conduit shield 68 and a column shield 69. The conduit shield 68 covers the respective conduits 59, 61, 64, 65, or portions thereof, from adjacent the input, output, and venting needles, 30, 32, 54, respectively, to adjacent the top 60a of the elution column 60b. The conduit shield 68 also covers the fillport needle 63 and the output filter 62. The conduit shield 68 defines internal passages for receiving and covering the respective components, while leaving the input, output, and venting needles 30, 32, 54 and the air filter 66 exposed. The conduit shield 68 may be a two-piece construction and may include (e.g., be made from or have in their construct) lead, tungsten, tungsten impregnated plastic, depleted uranium and/or another suitable radiation shielding material. Referring to FIGS. 14 AND 15, the column shield 69 defines a chamber (not shown) for receiving the elution column 60 and a lower portion 71 of the conduit shield 68 therein. The column shield 64 may be a one-piece construction and may include (e.g., be made from or have in their construct) lead, tungsten, tungsten impregnated plastic, depleted uranium and/or another suitable radiation shielding material.

Referring back to FIG. 1, the illustrated auxiliary shield assembly body 20 includes a top ring 72, a base 73, and a plurality of step-shaped or generally tiered, modular rings 74, which are disposed one over the other between the base 73 and the top ring 72. Substantially all or part of the illustrated auxiliary shield assembly body 20 may be made of one or more suitable radiation shielding materials, such as depleted uranium, tungsten, tungsten impregnated plastic, or lead. The modular aspect of the rings 74 may tend to enhance adjustment of the height of the auxiliary shield assembly body 20, and the step-shaped configuration may tend to contain some radiation that might otherwise escape through a linear interface between the modular rings. It is understood that the auxiliary shield assembly body 20 may be of other configurations. In one embodiment (FIG. 1B), an auxiliary shield cover 75 is receivable over the body 20. The cover 75 has a smooth exterior surface for ease of cleaning and to protect the outer surface of the body 20. The cover 75 may be formed from plastic (e.g., high-impact polypropylene) or other material.

Referring now to FIGS. 6-11, the radiation shielding lid 24 includes: a generally cylindrical lid body 76 having upper and lower surfaces, 77, 78, respectively; an elution tool opening 79; and an eluant vial opening 80. In one example (of which an exemplary method of making is explained in more detail below), the lid body 76 includes a radiation shielding core 124 that is overmolded with a plastic material 126, 128. As an example, the radiation shielding core 124 may include depleted uranium, tungsten, tungsten impregnated plastic, or lead. The upper and lower surfaces 77, 78, respectively, are generally planar, although the surfaces may be other than generally planar.

A male alignment structure, generally indicated at 81, is provided on the lower surface 78 of the lid body 76 to facilitate proper alignment of the lid 24 on the generator 12. More specifically, the male alignment structure 81 has a shape generally corresponding with the combined shape of the recessed portion 40 and the channel 42 of the generator 12 (together, these recessed portion 40 and the channel 42 constitute a female alignment structure) so that the male alignment structure mates with the generator in order to align the elution tool opening 79 with the output needle 32 and the eluant vial opening 80 with the input needle 30 and the venting needle 54. As such, it may be said that the lid 24 is keyed with the generator 12 (e.g., the cap 38 thereof) such that proper positioning of the lid 24 atop the generator 12 results in alignment of the respective openings 79, 80 with the corresponding needles 32, 30. The structure 81 enables only one position of the lid 24 relative to the generator 12. The illustrated male alignment structure 81 includes a wall 81a projecting outward from the bottom surface 78 and surrounding the elution tool opening 79 and the eluant vial opening 80. A plurality (e.g., a pair) of handles 82 on the upper surface 77 of the lid body 76 allows the radiopharmacist or technician to properly place the lid 24 on the generator 12 and remove the lid from the generator.

The elution tool opening 79 extends through the lid body 76 from the upper surface 77 through the lower surface 78 thereof. The elution tool opening 79 is sized and shaped for removably receiving the elution tool 16 therein. For example, in the illustrated embodiment, the elution tool opening 79 has a generally circular circumference that is substantially uniform along its axis. In one embodiment, the elution tool opening 79 has a diameter slightly larger than an outer diameter of the elution tool 16 such that the opening effectively aligns the septum (not shown) of the elution vial 17 (FIG. 4) with the output needle 32 as the elution tool is inserted into the opening. For example, the elution tool opening 79 may have a diameter that is from about 0.25 mm (0.01 in) to about 1.0 mm (0.04 in) larger than the outer diameter of the elution tool 16. In one embodiment, the elution tool opening 79 may have a diameter from about 46 mm (1.8 in) to about 48 mm (1.9 in), although it may alternatively have a diameter falling outside this range. Other shapes and sizes of the elution tool opening 79 may be appropriate; however, it tends to be preferred that the shape and size of the elution tool opening 79 be at least generally complimentary to the shape and size of the elution tool 16 being used with the radiation shielding lid 24 to reduce the likelihood of misalignment between the elution vial 17 and the output needle 32.

Figure 9:
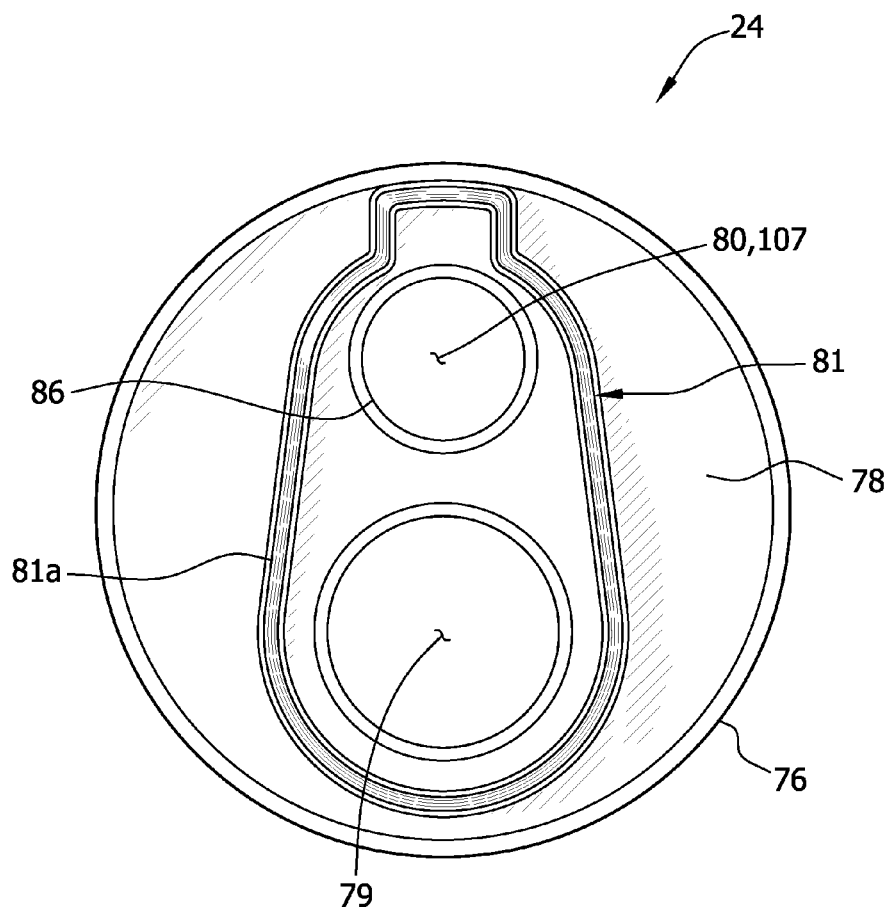
FIG. 9 is a bottom plan of the auxiliary shield assembly lid of FIG. 6.
Figure 10:
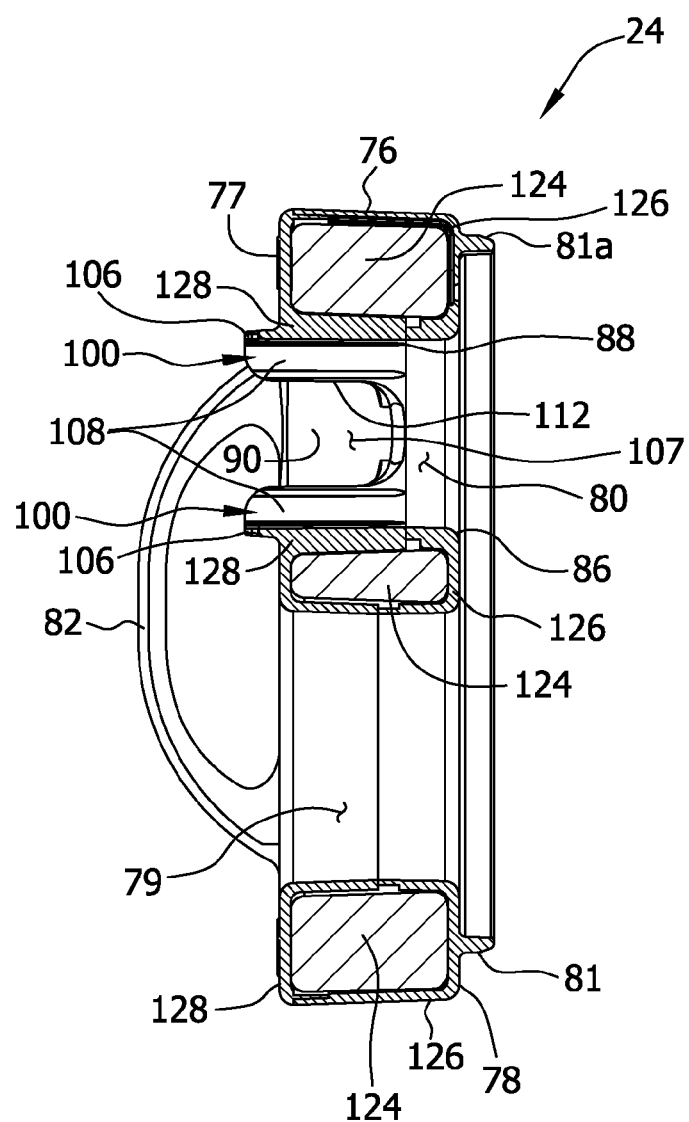
FIG. 10 is a cross section of the auxiliary shield assembly lid of FIG. 6 taken through line 10-10 in FIG. 8.

As shown in FIGS. 9 and 10, the eluant vial opening 80 is spaced apart and separate from the elution tool opening 79, and is sized and shaped for removably receiving an eluant vial 18 (FIG. 2), such as a vial containing saline or other eluants. In the illustrated embodiment (FIG. 10), the eluant vial opening 80 has a lower end 86 at the lower surface 78 of the lid body 76 and an upper end 88 intermediate the upper and lower surfaces 77, 78, respectively. In one example, the eluant vial opening 80 may have a diameter from about 34.0 mm (1.34 in) to about 34.5 mm (1.36 in), although it may alternatively have a diameter falling outside this range. As with the elution tool opening 79, other shapes and sizes of the eluant vial opening 80 may be appropriate; however, it tends to be preferred that the shape and size of the eluant vial opening 80 be at least generally complimentary to the shape and size of the eluant vial 18 being used with the radiation shielding lid 24 to reduce the likelihood of misalignment between the eluant vial 18 and the input needle 30 and venting needle 54.

Figure 8:
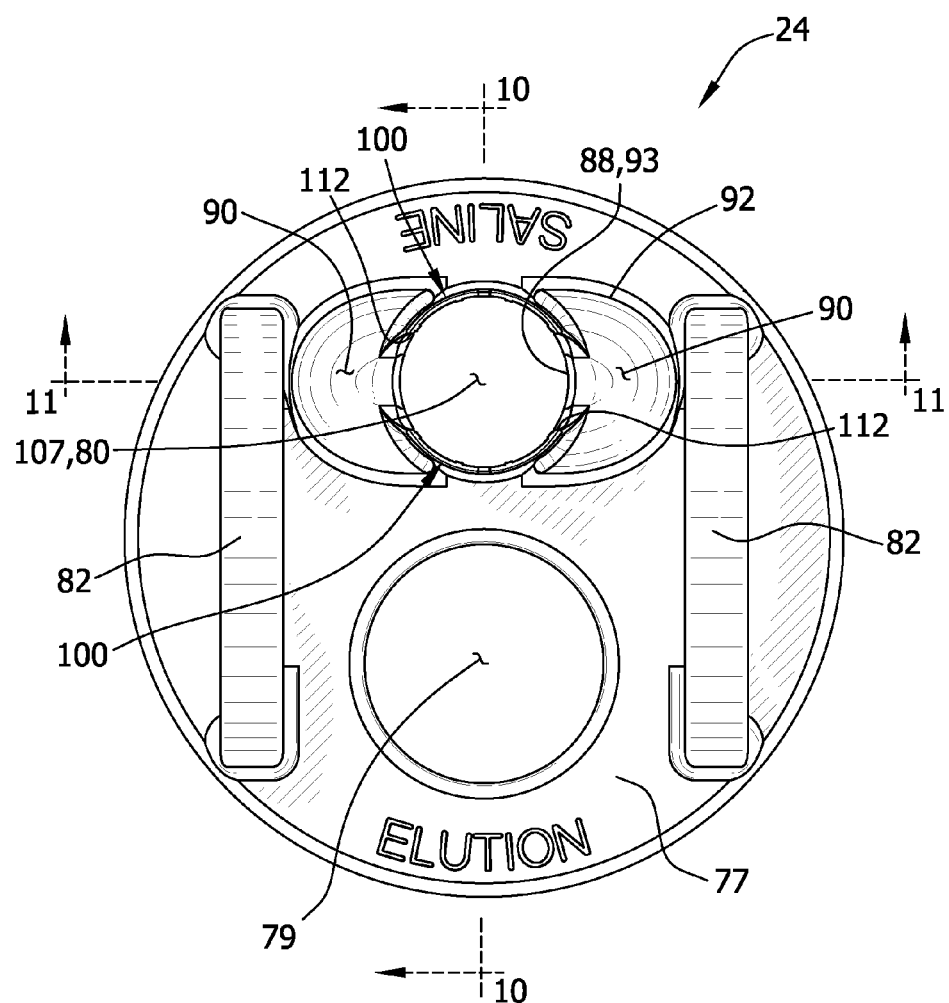
FIG. 8 is a top plan of the auxiliary shield assembly lid of FIG. 6.

Referring to FIGS. 2, 6, 8, and 11, the illustrated lid 24 has two finger recesses 90 formed in the upper surface 77 of the lid body 76, which are diametrically opposite one another with respect to the eluant vial opening 80. The finger recesses 90 are defined by respective recessed surfaces extending downward from the upper surface 77 of the lid body 76 to the eluant vial opening 80, and are sized and shaped to allow at least distal portions of two fingers of a radiopharmacist or other appropriate technician to enter the finger recesses. Recessed surfaces defining illustrated finger recesses 90 are curved and generally in the shape of a half-bowl such that the recessed surfaces lead the radiopharmacist's or technician's fingers toward the eluant vial opening 80. It is understood that in other embodiments the lid 24 may have a single finger recess, such as a finger recess that completely or partially surrounds the eluant vial opening 80, or more than two finger recesses. Referring to FIG. 8, each illustrated finger recess 90 has an upper edge 92 adjacent the upper surface 77 of the lid body 76 and a lower edge 93 that is coextensive with a portion of the upper end 88 of the eluant vial opening 80.

Figure 11:
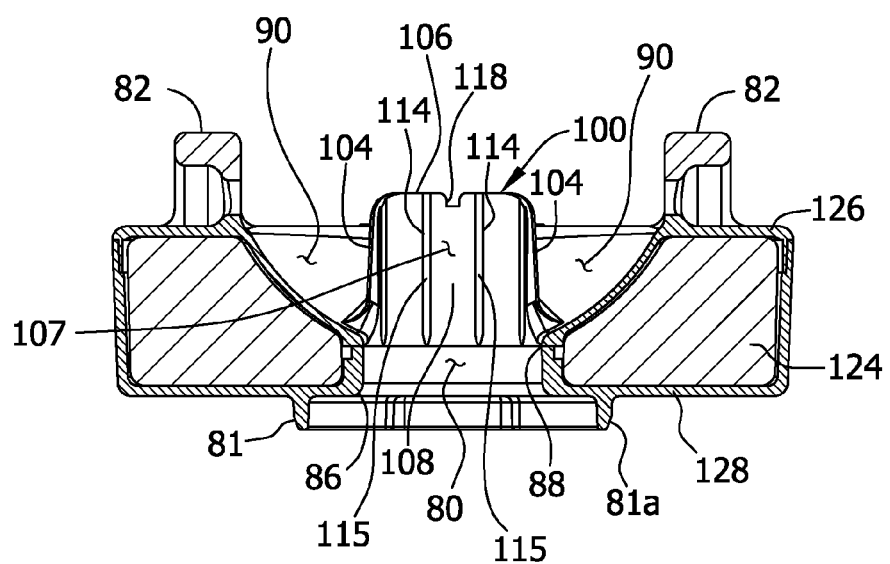
FIG. 11 is a cross section of the auxiliary shield assembly lid of FIG. 6 taken through line 11-11 in FIG. 8.

Referring to FIG. 11, the lid 24 of the auxiliary shield assembly 14 includes first and second alignment wings 100, each designated generally at reference numeral 100, extending upward from adjacent the upper end 88 of the eluant vial opening 80 within the finger recesses 90. Each of the first and second wings 100 has opposite sides 104, a top portion 106, and an inner surface 108 extending partially around a circumference of the upper end 88 of the eluant vial opening 80. In the illustrated embodiment, the top portion 106 of each of the wings 100 is disposed above the upper surface 77 of the lid body 76 (as seen best in FIGS. 7 and 10), and the inner surface 108 of each of the wings 100 is generally arcuate, although it is understood that the wings 100 may be of other shapes and relative dimensions. Together, the inner surfaces 108 of the wings 100 and the eluant vial opening 80 define a vial passageway 107 extending from the top portions 106 of the wings 100 through the lower surface 78 of the lid body 76.

The wings 100 preferably enable alignment of the eluant vial septum with the input needle 30 and venting needle 54 as the eluant vial 18 is inserted into the vial passageway 107. As such, the wings 100 preferably make it is less likely that the input needle 30 or venting needle 54 will contact the metal ring or other hard part of the vial and damage the needle. In one example, the inner surface 108 of each wing 100 may extend at least 45 degrees and less than 180 degrees around the circumference of the upper end 88 of the eluant vial opening 80. In other examples, the inner surface 108 of each wing 100 may extend at least 60 degrees, or at least 90 degrees, and less than 180 degrees around the circumference of the upper end 88 of the eluant vial opening 80. Other configurations of the wings 100 do not depart from the scope of the present disclosure.

To facilitate gripping of the eluant vial 18 during at least one of insertion of the vial into the vial passageway 107 and removal of the vial from the vial passageway, the respective adjacent sides 104 of the first and second wings 100 are spaced apart from one another about the eluant vial opening 80 to define gaps or first and second finger channels, each indicated at 112 (FIGS. 6 and 10), leading from the finger recesses 90 to the vial passageway. In the illustrated embodiment, the finger channels 112 are diametrically aligned, relative to the vial opening 80, with the finger recesses 90, and the respective sides 104 of the wings 100 extend into the associated finger recesses 90. Each of the first and second finger channels 112 are sized and shaped to allow at least the distal portion of one of the two fingers to enter the corresponding finger channel from the associated finger recess 90. For example, a minimum width of each of the finger channels 112 (i.e., the distance between the respective adjacent sides 104 of the first and second wings 100) may measure from about 19 mm (0.75 in) to about 21 mm (0.83 in), and more specifically, from about 19.0 mm (0.748 in) to about 19.6 mm (0.776 in), although the minimum width of each finger channel may fall outside this range. Thus, the finger channels 112 allow the radiopharmacist or technician to grip the eluant vial 18, such as by using his/her thumb and forefinger, during at least one of insertion of the vial in the vial passageway 107 and removal of the vial from the vial passageway.

In the illustrated embodiment (FIGS. 8, 10, and 11), a diameter of a portion of the vial passageway 107 defined by the inner surfaces 108 of the wings 100 tapers from the top portions 106 of the wings toward the eluant vial opening 80. Tapering the inner surfaces 108 of the wings 100 facilitates molding of the wings when overmolding the lid 24 in one example, as described below. Although this diameter of the vial passageway 107, as defined by the inner surfaces 108, tapers along the length of the passageway, a plurality of alignment ribs 114 are provided on the inner surfaces to define an effective inner diameter of the vial passageway that is substantially uniform along the length of the passageway. The ribs 114 are spaced apart from one another between the sides 104 of the wings and extend longitudinally along the respective wings 100. The wings 100 project inwardly, generally toward a centerline of the passageway 107, such that each rib 114 has a terminal, guiding surface 115 (FIG. 11) generally facing the centerline of the passageway. Each guiding surface 115 is uniformly spaced from the centerline of the vial passageway 107 along its length. In other words, the guiding surface 115 of each rib 114 does not taper or flare with respect to the axis of the vial passageway 107. Through this configuration, the guiding surfaces 115 effectively align the elution vial 18 with the input needle 30 and venting needle 54 even though the inner surfaces 108 of the wings 100 are tapered. The ribs 114 have depths projecting into the vial passageway 107 relative to the respective inner surfaces 108. Because the diameter of the vial passageway 107 defined by the inner surfaces 108 of the wings 100 tapers, yet the guiding surfaces 115 do not taper or flare relative to the centerline of the vial passageway, the depths of the ribs relative to the respective inner surfaces 108 taper toward the eluant vial opening 80. The wings 100 may not include the ribs 114 without departing from the scope of the present disclosure.

As illustrated in FIG. 3, a bottom 116 of the eluant vial 18 lies slightly below or at the top portions 106 of the wings 100 when the eluant vial is received in the vial passageway 107 and fluidly connected to the input needle 30. Notches 118 in the top portions 106 of the wings 100 allow the radiopharmacist or technician to view the eluant vial 18 in the passageway without having to position his/her head above the upper surface 77 of the lid 24.

In one example, the auxiliary shield lid 24 may be formed by a two-step overmolding process. In such a process, a radiation shielding core 124 (FIG. 10)—which may include a suitable radiation shielding material such as depleted uranium, tungsten, tungsten impregnated plastic, or lead—is provided. The core 124 may be generally disk-shaped, having first and second openings, which will form the elution tool and eluant vial openings, 79, 80, respectively, and recesses, which will form the finger recesses 90. A first molded part is molded with a first thermoplastic material 126 to form the bottom surface 78, the male alignment structure 81, and the sidewall of the body 76, and at least lower portions of the elution tool opening 79 and the eluant vial opening 80. Next, the core 124 is placed into the first molded part. Finally, this assembly is overmolded with a second thermoplastic material 128 to form the top surface 77, the handles 82, the finger recesses 90, the wings 100, and an upper portion of at least the elution tool opening 79. The first and second thermoplastic materials 126, 128, respectively, may include polypropylene and polycarbonate, or other material, and the first and second thermoplastic materials may be of the same material. Other methods of making the auxiliary shield lid 24 may be used.

Referring to FIGS. 18-21, an eluant shield 136 of the elution system 10 is positionable over the eluant vial 18 when the vial is received in the eluant vial opening 80 in the lid 24 and fluidly connected to the generator 12 to inhibit exposure of the radiopharmacist or technician to radiation when the eluant is fluidly connected to the generator (e.g., during and after an elution process). The eluant shield 136 has a top 138, an opposing bottom 140, and a cavity 142 extending from the bottom toward the top. A pair of shielding wings 144 at the bottom 140 of the eluant shield 136 partially surround the cavity 142. The shielding wings 144 are sized and shaped to fit snugly within the finger recesses 90 in the lid 24 so that the top portions 106 of the alignment wings 100 are received in the cavity 142 of the eluant shield 136 and the shielding wings 144 oppose the sides 104 of the alignment wings and the finger channels or gaps 112 between the sides of the alignment wings. As such, substantially an entirety of the eluant vial 18 is surrounded by radiation shielding material of either the lid 24 or the eluant shield 136. More specifically, when the eluant shield 136 is positioned on the lid 24, substantially the entirety of the eluant vial 18 is surrounded by a suitable radiation shielding material, such as depleted uranium, tungsten, tungsten impregnated plastic, or lead.

In one example, the eluant shield 136 may be formed by a two-step overmolding process. In such a process, a radiation shielding core 124, which may include a suitable radiation shielding material such as depleted uranium, tungsten, tungsten impregnated plastic, or lead—is provided. The core is substantially the same shape as the eluant shield in finished form, including a pair of shielding wings and a cavity. A first molded part is molded with a first thermoplastic material to form the top 138. Next, the core is placed into the first molded part. Finally, this assembly is overmolded with a second thermoplastic material to form the bottom 140, the shielding wings 144, and the cavity 142. The first and second thermoplastic materials, respectively, may include polypropylene and polycarbonate, or other material, and the first and second thermoplastic materials may be of the same material. Other methods of making the eluant shield 136 may be used.

Referring to FIGS. 22-33, a second embodiment of an elution tool 150 is generally indicated at reference numeral 150. This elution tool 150 includes a body, generally indicated at 152, having a top 154, and opposing bottom 156; and a lid, generally indicated at 158, hingedly secured to the top of the elution tool body. As explained in more detail below, a dispensing cap 160 (FIG. 22) is removably securable to the bottom 156 of the elution tool body 152 for configuring the elution tool in a dispensing tool configuration, and a storage cap 162 (FIG. 23) is removably securable to the bottom of the elution tool body for configuring the elution tool into a storage tool configuration. In generally, the dispensing cap 160 and the storage cap 162 are interchangeably securable to the elution tool body 152. In the illustrated embodiment, neither the dispensing cap 160 nor the storage cap 162 are secured to the elution tool body 152 when then elution tool 150 is inserted in the auxiliary shield and the elution vial 17 in the elution tool is fluidly connected to the generator 12.

The elution tool body 152 is sized and shaped to be slidably receivable in the elution tool opening 79 in the auxiliary shield lid 24. The body 152 has an upper longitudinal portion 163 having first outer diameter that defines an annular stop surface 164 to inhibit the top 154 of the body from entering the elution tool opening 79 in the auxiliary shield lid 24. A lower longitudinal portion 166 of the body 152, having a second outer diameter that is less than the first outer diameter, is receivable in the dispensing and shielding caps 160, 162, respectively, as explained in more detail below. An intermediate longitudinal portion 168 of the body 152, having an outer diameter that is less than the first outer diameter and greater than the second outer diameter OD₂, is sized and shaped to be slidably receivable in the elution tool opening 79. The elution tool body 152 may include (e.g., be made from or have in their construct) lead, tungsten, tungsten impregnated plastic, depleted uranium and/or another suitable radiation shielding material.

The elution tool body 152 is configured to receive the elution vial 17 therein. In particular, the elution tool body 152 has a vial chamber 170 (FIG. 33) defined therein extending from an opening 172 in the top 154 of the elution tool body to an opposing access opening 174 in the bottom thereof. The top opening 172 is sized and shaped to allow the elution vial 17 to be inserted into and removed from the vial chamber 170, and the vial chamber has a size and shape generally corresponding to the size and shape of the elution vial such that the elution vial fits generally snugly within the chamber. The bottom 156 of the elution tool body 152 defines an annular internal surface 178 surrounding the access opening 174. When the elution vial 17 is received in the vial chamber 170, the metal ring 17b of the vial contacts the internal surface 176 so that the septum 17a is aligned with the access opening 174. Accordingly, when the elution tool 150 is inserted into the elution tool opening 79 in the lid 24, the output needle 32 enters the access opening 174 and pierces the septum 17a.

The elution tool lid 158 is hingedly secured to the elution tool body 152 and configurable between an open or exposed position (FIG. 24), in which the top opening 172 is exposed and the elution vial 17 can be inserted into and removed from the vial chamber 170, and a closed or occluded position (FIGS. 25-28), in which the top opening is occluded and the elution vial is retained in the vial chamber. The elution tool lid 158 includes a generally planar or disk-shaped lid body 178 that is receivable in a lid recess 180 defined in the top 154 of the elution tool body 152 when the lid is in the closed position. The lid body 178 has a lower face 178a that seats on an inner annular flange or lid seat 182 of the lid recess 180, and an upper face 178b that is substantially coplanar with the top 154 of the elution tool body 152 when the lid 158 is in a closed position. The upper face 178b of the lid body 178 has a plurality of gripping slots 179 formed therein to provide a gripping region for the radiopharmacist or technician when opening and closing the lid, as explained in more detail below. For reasons which are apparent from the below description, the elution tool lid 158 has a generally circular periphery, and the lid recess 180 and the lid seat 182 have generally oblong peripheries. Moreover, the elution tool lid 158 is sized and shaped to allow for movement of the lid along the major axis of the lid recess 180 when the lid is seated on the lid seat 182. The elution tool lid body 178, may include (e.g., be made from or have in their construct) lead, tungsten, tungsten impregnated plastic, depleted uranium and/or another suitable radiation shielding material.

Referring to FIGS. 22-28, the illustrated elution tool 150 includes a hinged lid connection, generally indicated 186, and a latching mechanism, generally indicated at 188, for releasable locking the lid 158 in the closed position. The hinged lid connection 186 includes a hinge connector 190 extending radially or laterally outward from the periphery of the lid body 178, and a hinge pin 192, adjacent the periphery of the top 154 of the elution tool body 152, to which the hinge connector is coupled. The hinge connector 190 defines a slot 194 in which the hinge pin 192 is received to allow both rotation of the hinge connector (and the lid 158) about the hinge pin, and limited transverse, linear movement of the hinge connector (and the lid) relative to the hinge pin. The latching mechanism 188 includes a latching member 194 extending radially or laterally outward from the periphery of the lid body 178, generally diametrically opposite the hinge connector 190. The latching member 194 includes a tongue 196 that is slidably receivable in a latching groove 198 adjacent the periphery of the top 154 of the elution tool body 152. A detent 200 (e.g., a ball detent) on the elution tool body 152 extends into the latching groove 198 and releasably engages the latching member 194 (e.g., an underside of the latching member) as the tongue 196 is slid into the latching groove to inhibit the latching member from inadvertently withdrawing (e.g., sliding back out) from the latching groove.

To lock the lid 158 in the closed position (FIGS. 27 and 28), the radiopharmacist or technician can rotate the lid about the hinge pin 192 to the closed position such that the lid body 178 is seated on the lid seat 182 of the elution tool body 152. Once seated, the slot 194 in the hinge connector 190 allows the radiopharmacist or technician to move the lid 158 linearly toward the latching groove 198, whereby the tongue 196 can be slid into the latching groove 198. For example, while holding the elution tool 150 using one hand, the radiopharmacist or technician may contact the upper face 178b of the lid body 178 (more specifically, the region defined by the gripping slots 179) with his/her thumb to rotate the lid 158 to its closed position and then linearly slide the lid toward the latching groove 198. As the latching member 194 slides over the ball detent 200, the ball detent deflects and pushes against the latching member. Once the tongue 196 is received in the latching groove 198, the lid 158 is releasably locked in the closed position. The lid 158 may be unlocked (FIGS. 25 and 26) by the radiopharmacist or technician using his/her thumb to slide the lid away from the latching groove 198, against the pushing force of the ball detent, so that the tongue 196 is withdrawn from the latching groove 198. Once unlocked, the lid 158 can be rotated to the open position. It is understood that the lid 158 may be releasably lockable in the closed position in other ways, and other ways of retaining the elution vial 17 in the elution tool 150 do not depart from the scope of the present disclosure.

Figure 22:
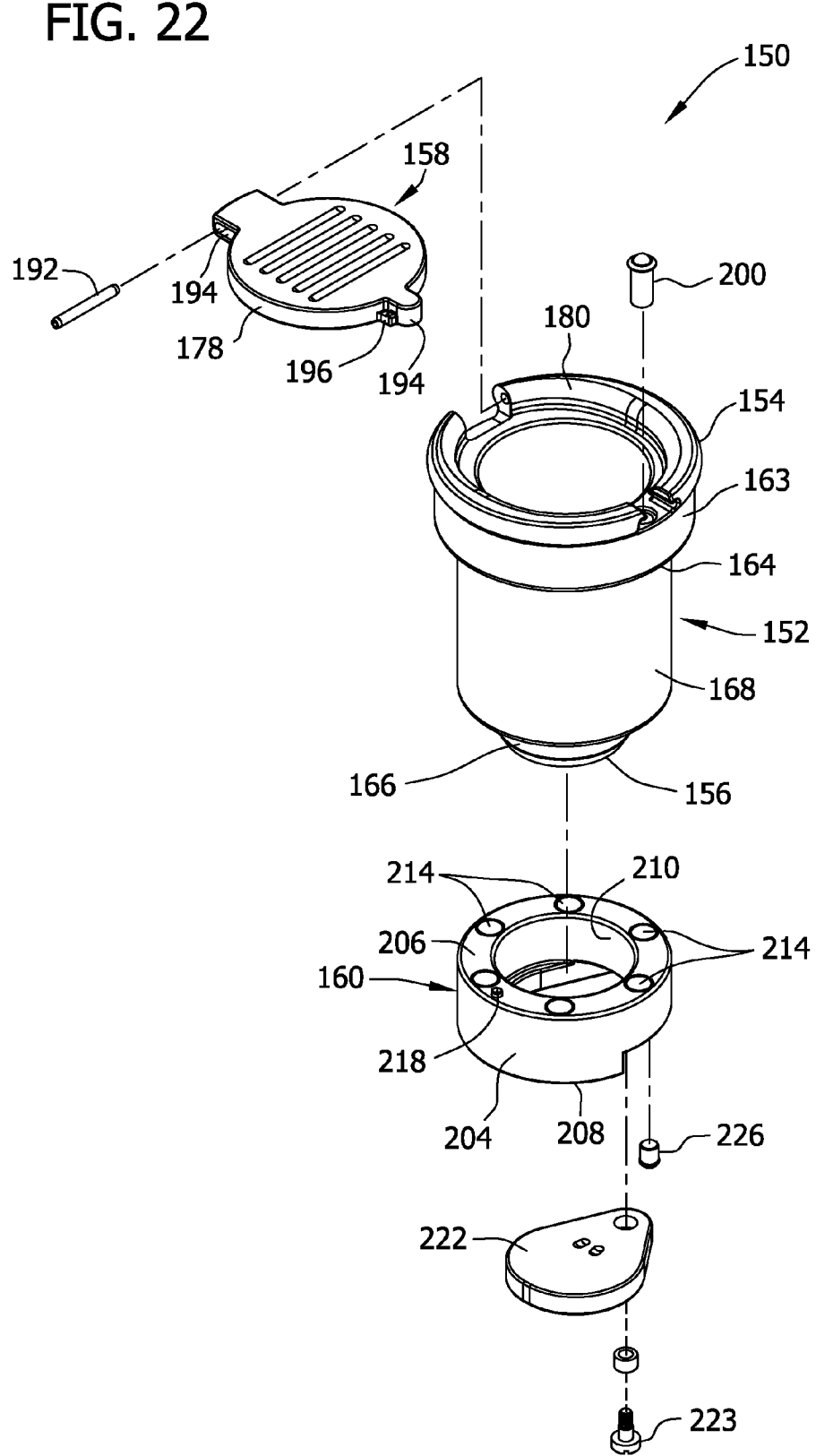
FIG. 22 is an exploded perspective of a second embodiment of an elution tool, including a dispensing cap removed from a body of the elution tool.

As disclosed above, dispensing cap 160 is removably securable to the lower longitudinal portion 168 of the elution tool body 152, such as shown in FIG. 22, to configure the elution tool in the dispensing configuration. In the dispensing configuration, the elution tool 150 can be used as a dispensing tool, whereby the radiopharmacist or technician can hold the elution tool and withdrawal a quantity of radiopharmaceutical from the elution vial 17 housed in the elution tool without removing the dispensing cap 160. The dispensing cap 160 includes a body 204 (e.g., a generally cylindrical body) having a top 206 and a bottom 208. The dispensing cap body 204 defines a socket 210 extending from the top 206 toward the bottom 208 thereof that is sized and shape for receiving the lower longitudinal portion 166 of the elution tool body 152. The socket 210 has an open top end to allow insertion of the lower longitudinal portion 166 of the elution tool body 152 into the socket, and an access opening 212 at the bottom 208 of the dispensing cap body 204 that is alignable with the access opening 174 in the elution tool body 152 to provide access to the septum 17b of the elution vial 17 in the chamber 170 of the elution tool body 152.

Referring to FIG. 22, the dispensing cap 160 includes a plurality of magnetic couplers 214 attached to dispensing cap body 204 and surrounding the socket 210 for releasably securing the dispensing cap to the elution tool body 152 when the lower longitudinal portion 166 of the elution tool body is received in the socket. The magnetic couplers 214 are magnetically attracted to an annular coupler surface 216 of the elution tool body 152 that is in opposing relationship with the magnetic couplers when the lower longitudinal portion 166 of the elution tool body is received in the socket 210 of the dispensing cap 160. In another embodiment, the elution tool body 152 may include magnetic couplers that are magnetically attracted to the magnetic couplers (or some other component or structure) of the dispensing cap body 204. The dispensing cap 160 also includes a locking pin 218 extending longitudinally outward from the top 206 of the dispensing cap body 204. The locking pin 218 is alignable with and receivable in a locking cavity 220 in the annular coupler surface 216 of the elution tool body 152 to inhibit the dispensing cap 160 from rotating about the elution tool body. In one example of securing the dispensing cap 160 to the elution tool body 152, the radiopharmacist or technician may insert the lower longitudinal portion 166 of the elution tool body 152 into the socket 210 of the dispensing cap 160 and then rotate the dispensing cap about the elution tool body (or vice versa) until the locking pin 218 aligns with and enters the locking cavity 220. The dispensing cap 160 may be removably securable to the elution tool body 152 in other ways.

The dispensing cap 160 includes a dispensing lid 222 pivotably secured to the bottom 208 of the dispensing cap body 204 by a pivot pin 223 (e.g., a pivot bolt) for selectively opening and closing the access opening 212 of the socket 210 and for providing suitable radiation shielding when the elution vial 17 is received in the elution tool 150. More specifically, the dispensing lid 222 is received in a recess 224 formed in the bottom 208 of the dispensing cap body 204, and is pivotable about a pivot axis defined by the pivot pin 223 that is generally parallel to the longitudinal axis of the elution tool 150. The dispensing lid 222 is pivotable between a non-dispensing position (FIGS. 29 and 30), in which the dispensing lid is aligned with and opposing (i.e., covering) the access opening 212 of the socket 210, and a dispensing position (FIGS. 30 and 31), in which the dispensing lid is at least partially misaligned with the access opening (i.e., the access opening is at least partially uncovered) to allow access to the septum 17b of the elution vial 17. A detent 226 (e.g., a ball detent) on the bottom 208 of the dispensing cap body 204 releasable locks the dispensing lid 222 in the non-dispensing position. Moreover, when the dispensing lid 222 is moved to the dispensing position, the detent 226 is removably receivable in one of a plurality of slots (e.g., three slots, not shown) formed on an underside of the dispensing lid. Accordingly, the dispensing lid 222 is releasably lockable in a selected one of a plurality of dispensing positions, each providing a different degree to which the lid is open.

To position the dispensing lid 222 in the dispensing position and provide access to the elution vial 17 in the elution tool 150 when the dispensing cap 160 is secured to the elution tool, a radiopharmacist or technician can hold the elution tool in one hand and use his/her thumb to grip the dispensing lid and swing (i.e., rotate) the dispensing lid about the pivot pin 223 and away from the access opening 212 in the dispensing cap. As the radiopharmacist or technician swings the dispensing lid 222 open, the detent 226 resiliently deflects to allow the dispensing lid to slide over the detent. The radiopharmacist or technician may continue to rotate the dispensing lid 222 until the lid is at a selected dispensing position and the detent 226 enters one of the slots (not shown) on the underside of the lid. With the dispensing lid 222 in a selected dispensing position, the radiopharmaceutical in the elution vial 17 is accessible to the radiopharmacist or technician, in that the radiopharmacist or technician can insert a dispensing needle of a syringe (not shown) through the access openings 212, 174 in the respective dispensing cap 160 and the elution tool body 150 and into the elution vial 17, by piercing the septum 17b, to withdraw a desired quantity of radiopharmaceutical from the elution vial. After withdrawing the desired quantity of radiopharmaceutical, the radiopharmacist or technician can position the dispensing lid 222 in the non-dispensing position by rotating or swinging the lid toward the access opening 212, whereby the detent 226 deflects as the lid slides toward the access opening. A wall 228 partially defining the recess 224 in the dispensing cap 160 acts as a stop for inhibiting the lid from sliding past the access opening 212 as the lid being closed.

The dispensing lid 222 may include (e.g., be made from or have in their construct) lead, tungsten, tungsten impregnated plastic, depleted uranium and/or another suitable radiation shielding material. In contrast, the dispensing cap body 204 may be formed from a suitable material, such as aluminum, plastic or other corrosion-resistant, lightweight material, or other material that has a density less than the density of suitable radiation shielding, such as that provided by lead, tungsten, tungsten impregnated plastic, depleted uranium. The dispensing cap body 204 does not need to provide suitable radiation shielding, such as that provided by lead, tungsten, tungsten impregnated plastic, depleted uranium and/or another suitable radiation shielding material, because such suitable radiation shielding is provided by the elution tool body 152. Accordingly, the dispensing cap 160 does not add a significant amount of weight to the elution tool 150 so that the elution tool may be suitably used as a dispensing tool for the radiopharmacist or technician.

Figure 23:
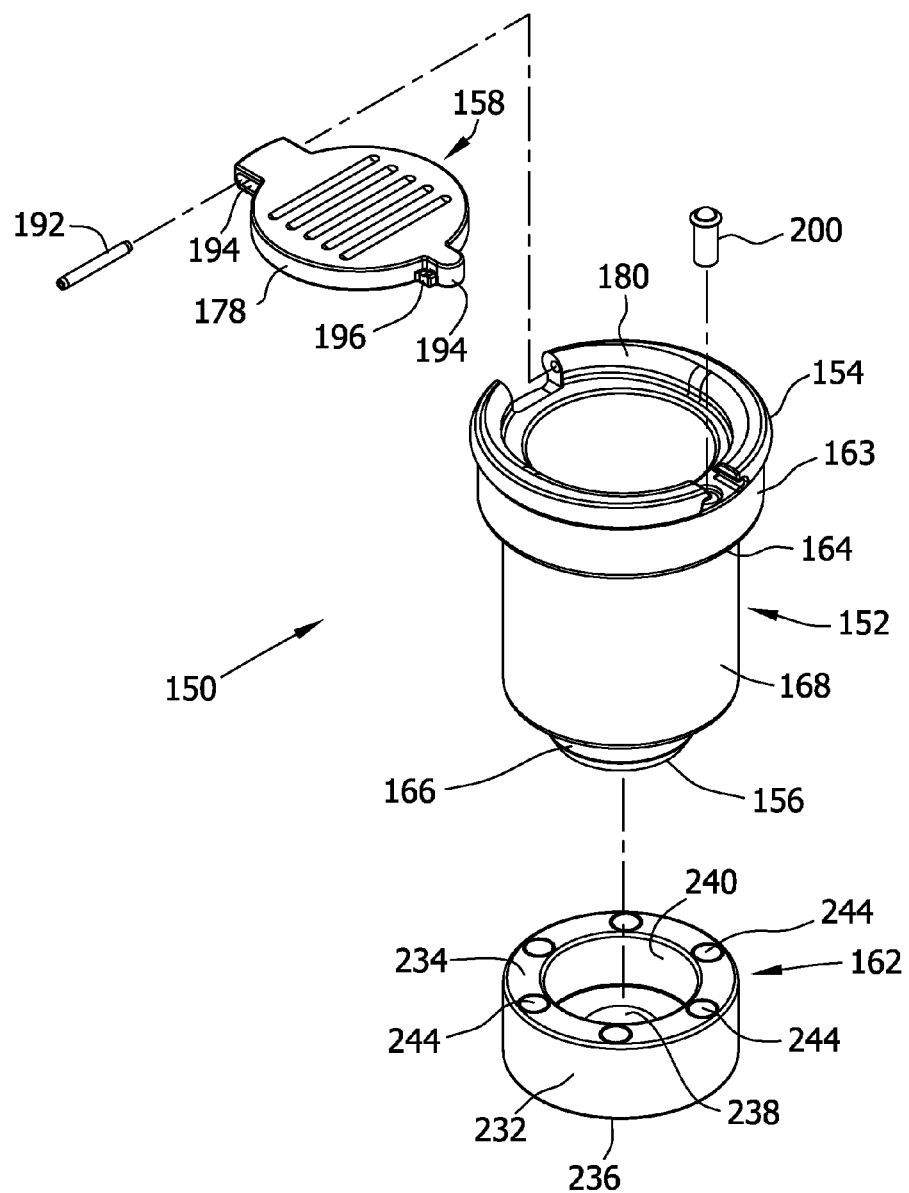
FIG. 23 is similar to FIG. 23, but with a storage cap removed from the body of the elution tool.
Figure 24:
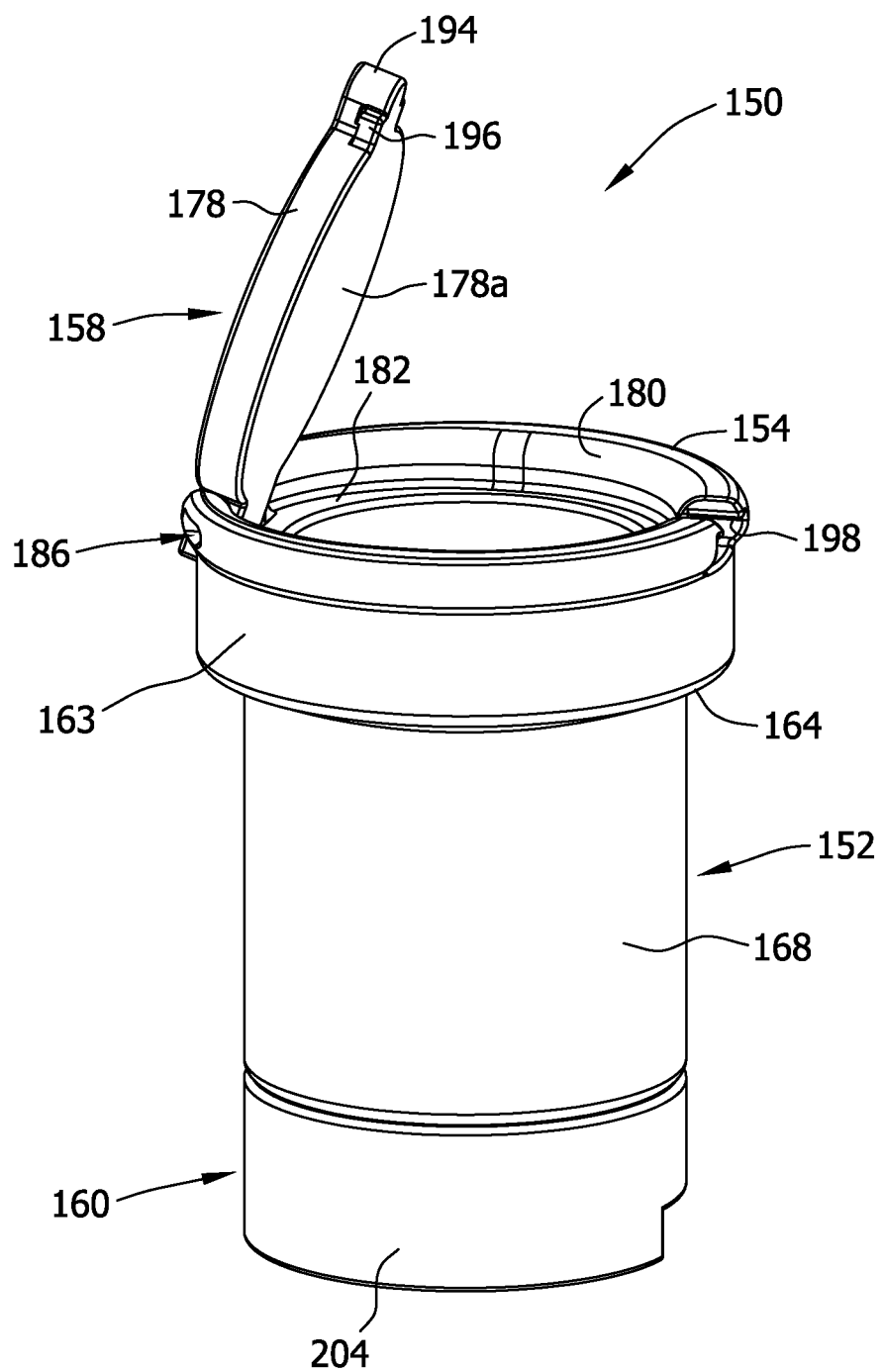
FIG. 24 is a perspective of the second embodiment of the elution tool including the dispensing cap, with a lid of the elution tool in an open position.
Figure 25:
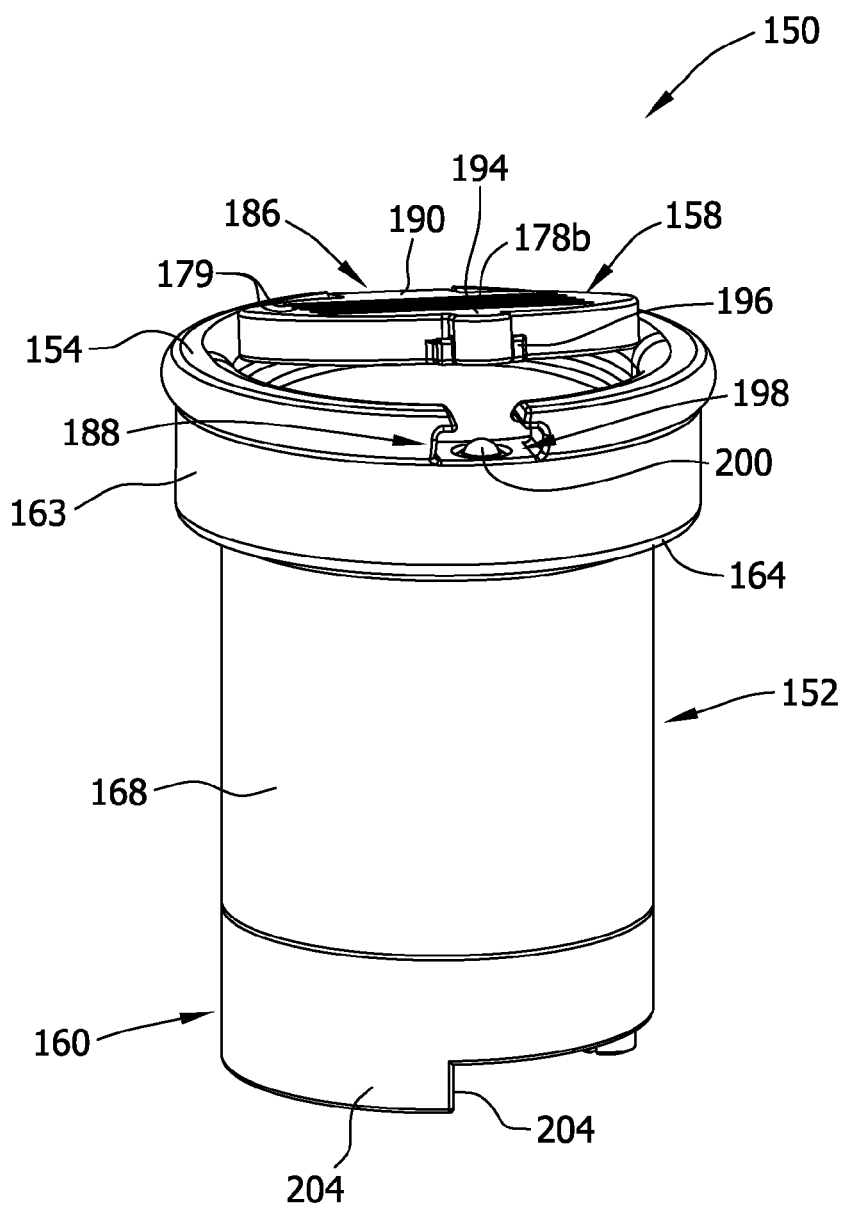
FIG. 25 is a perspective of the second embodiment of the elution tool including the dispensing cap, with the lid of the elution tool in a closed, unlocked position.
Figure 26:
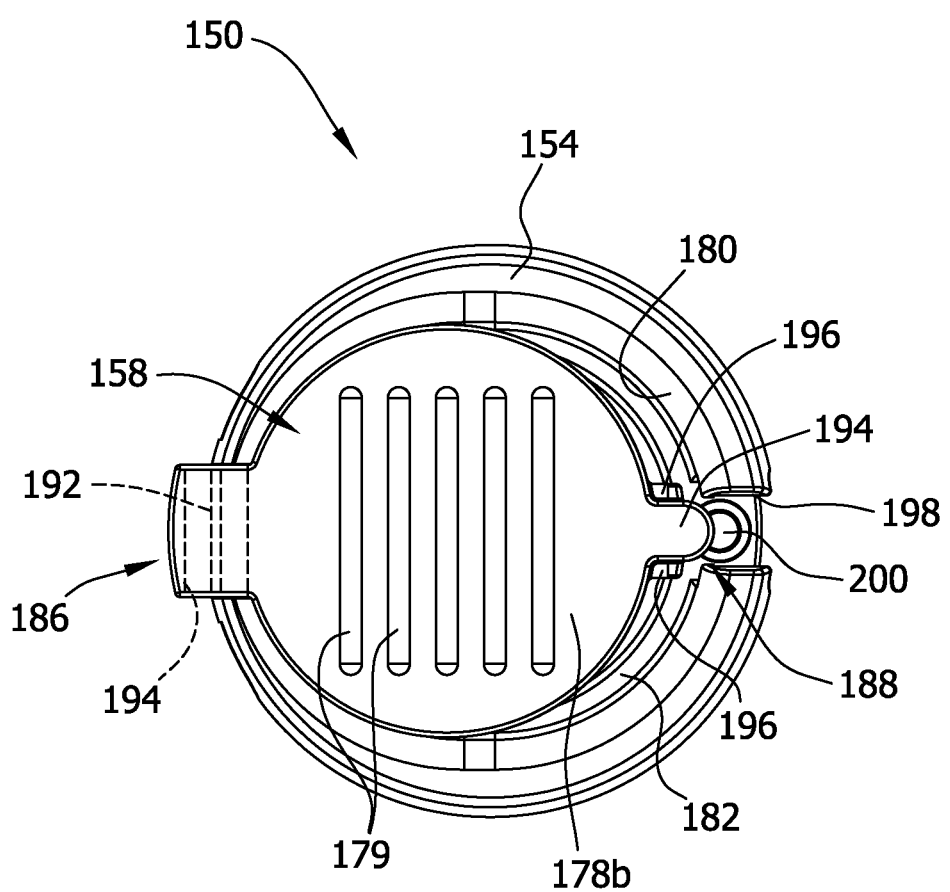
FIG. 26 is a top plan of the second embodiment of the elution tool including the dispensing cap, with the lid of the elution tool in a closed, unlocked position.
Figure 27:
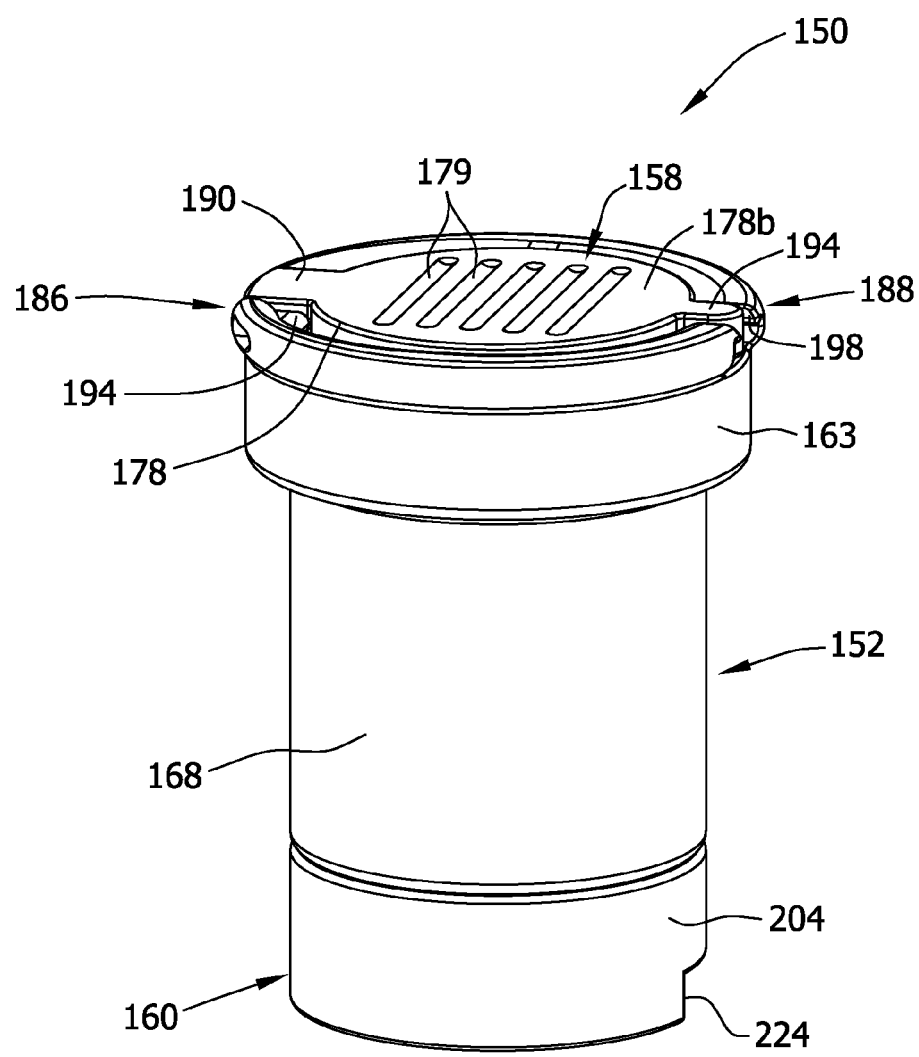
FIG. 27 is a perspective of the second embodiment of the elution tool including the dispensing cap, with the lid of the elution tool in a closed, locked position.
Figure 28:
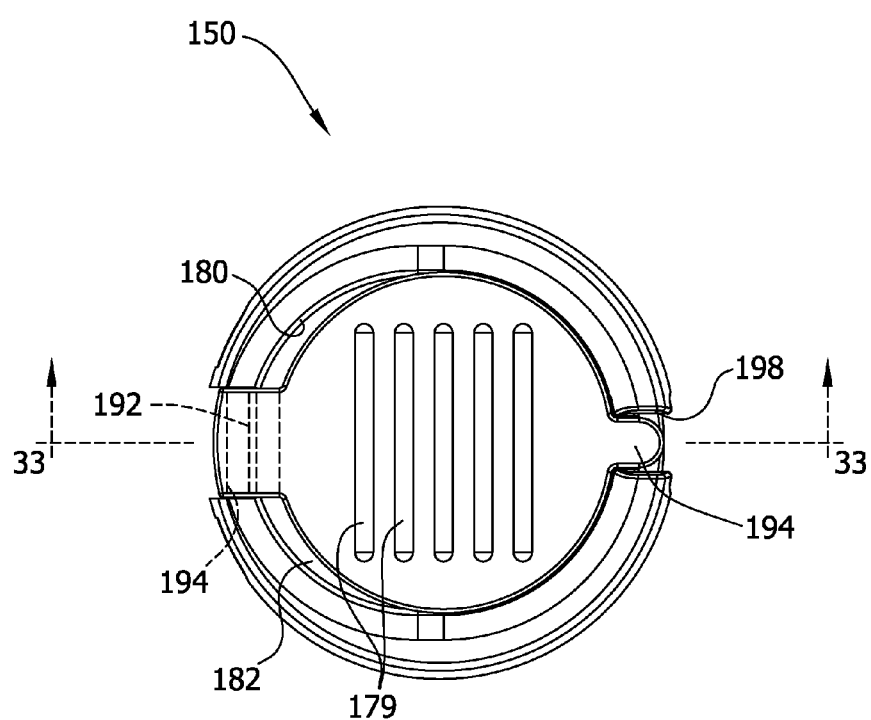
FIG. 28 is a top plan of the second embodiment of the elution tool including the dispensing cap, with the lid of the elution tool in a closed, locked position.
Figure 29:
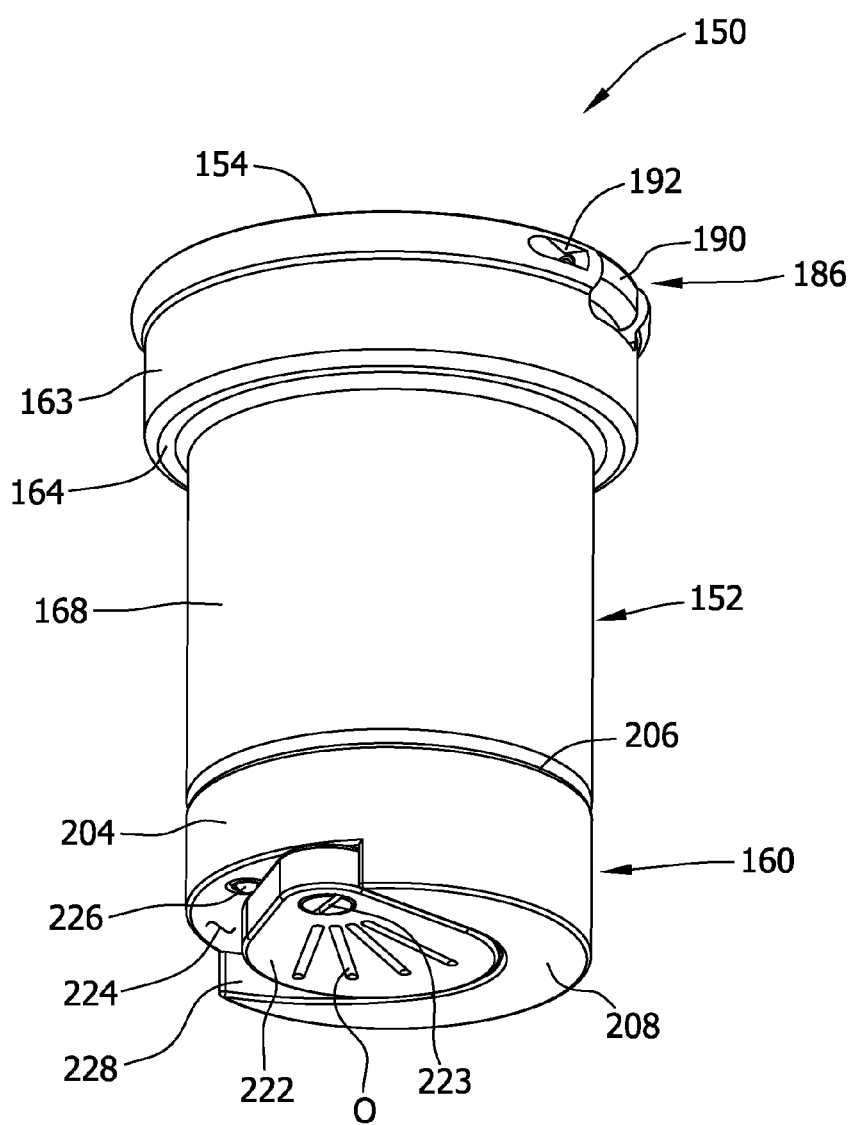
FIG. 29 is a bottom perspective of the second embodiment of the elution tool including the dispensing cap, with a dispensing lid of the dispensing cap in a closed position.
Figure 30:
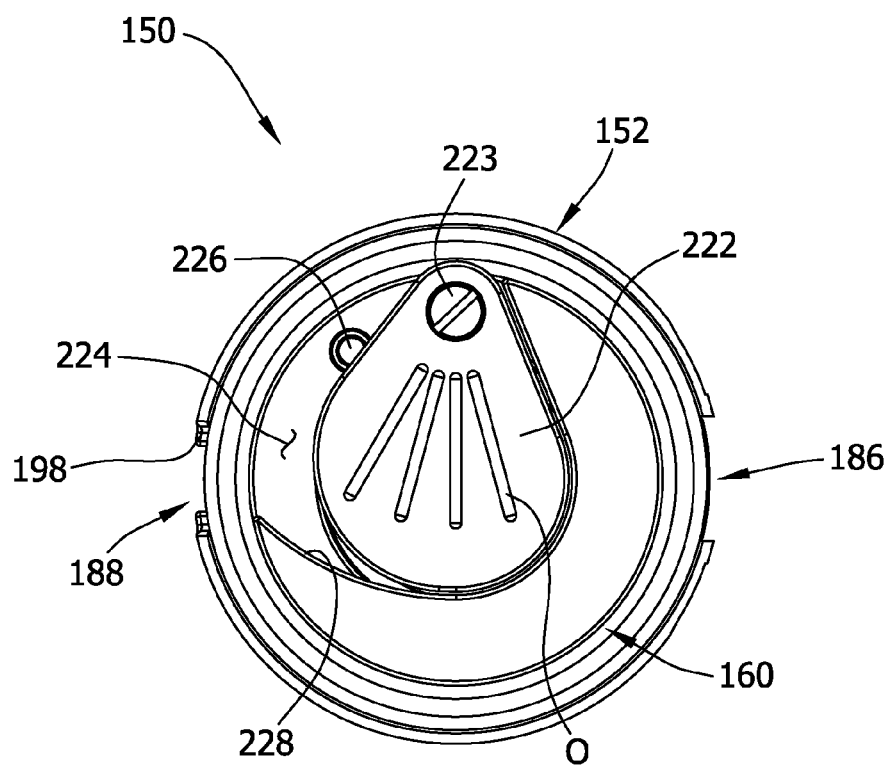
FIG. 30 is a bottom plan of the second embodiment of the elution tool including the dispensing cap, with a dispensing lid of the dispensing cap in a closed position.
Figure 31:
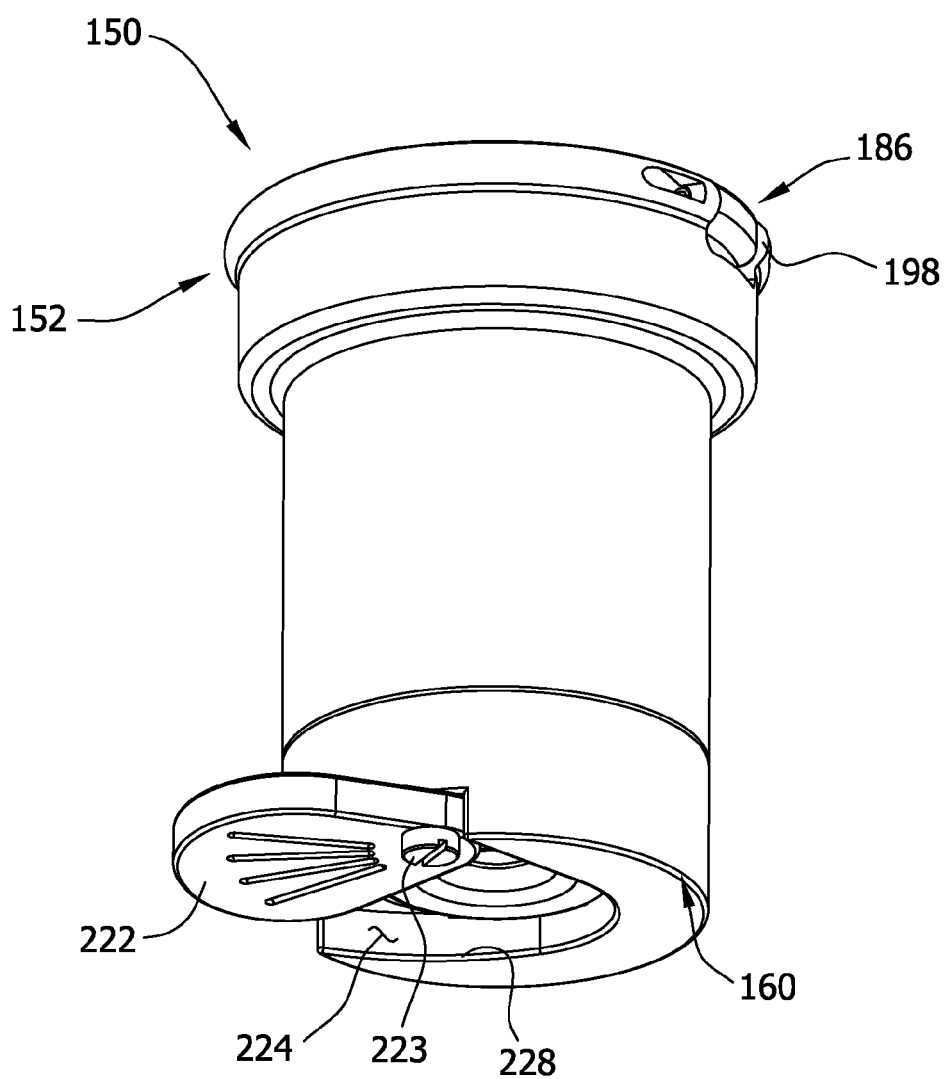
FIG. 31 is a bottom perspective of the second embodiment of the elution tool including the dispensing cap, with a dispensing lid of the dispensing cap in an open position.
Figure 32:
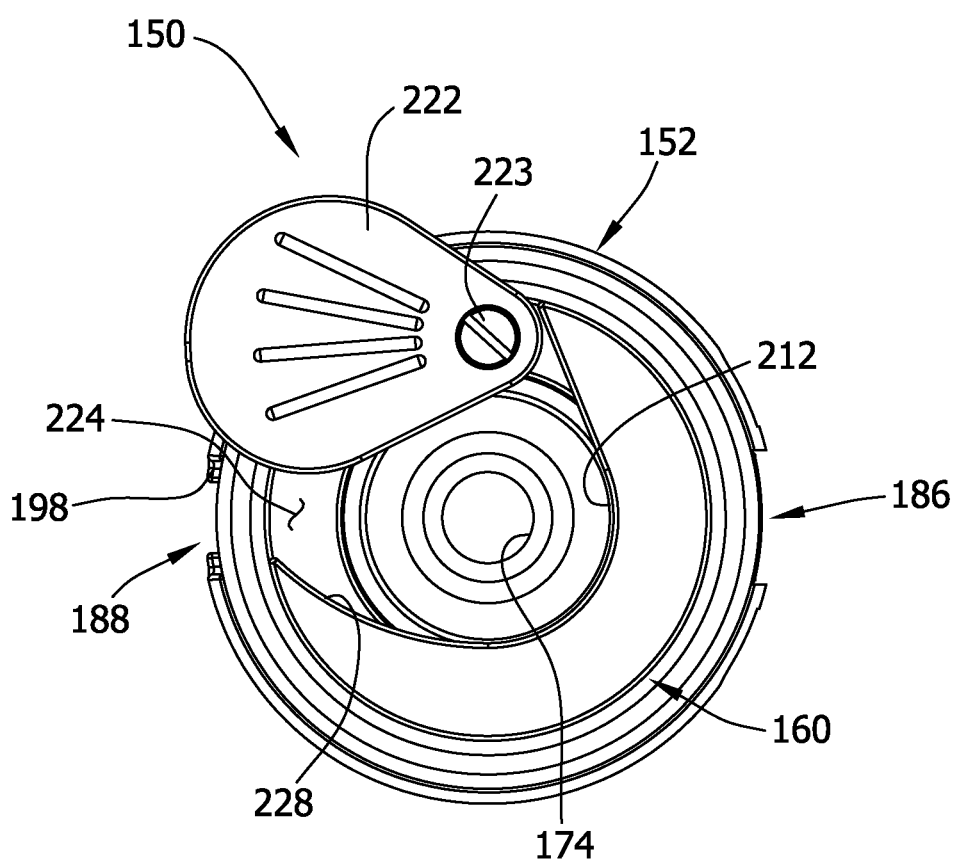
FIG. 32 is a bottom plan of the second embodiment of the elution tool including the dispensing cap, with a dispensing lid of the dispensing cap in an open position.
Figure 33:
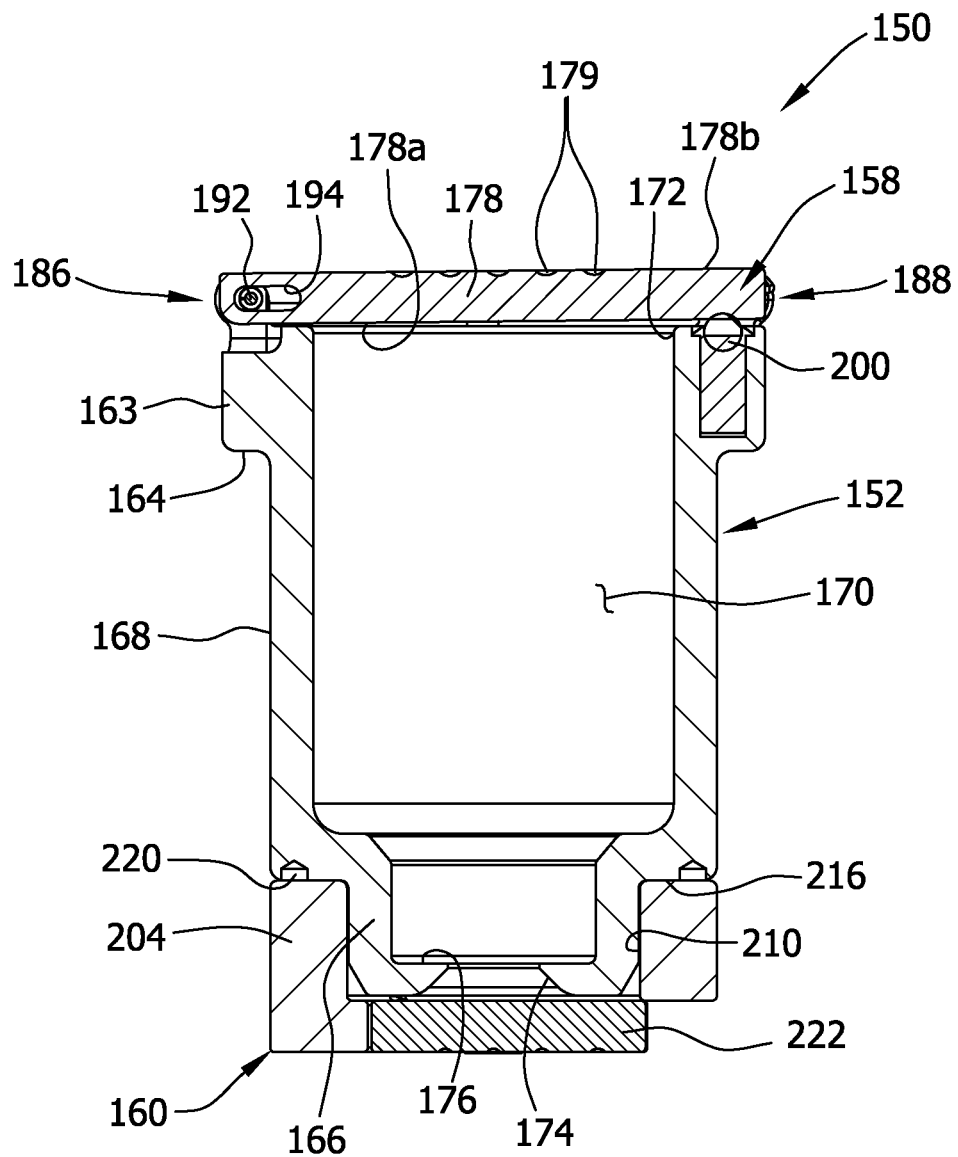
FIG. 33 is a sectional view of the elution tool taken through the line 33-33 in FIG. 28.
Figure 34:
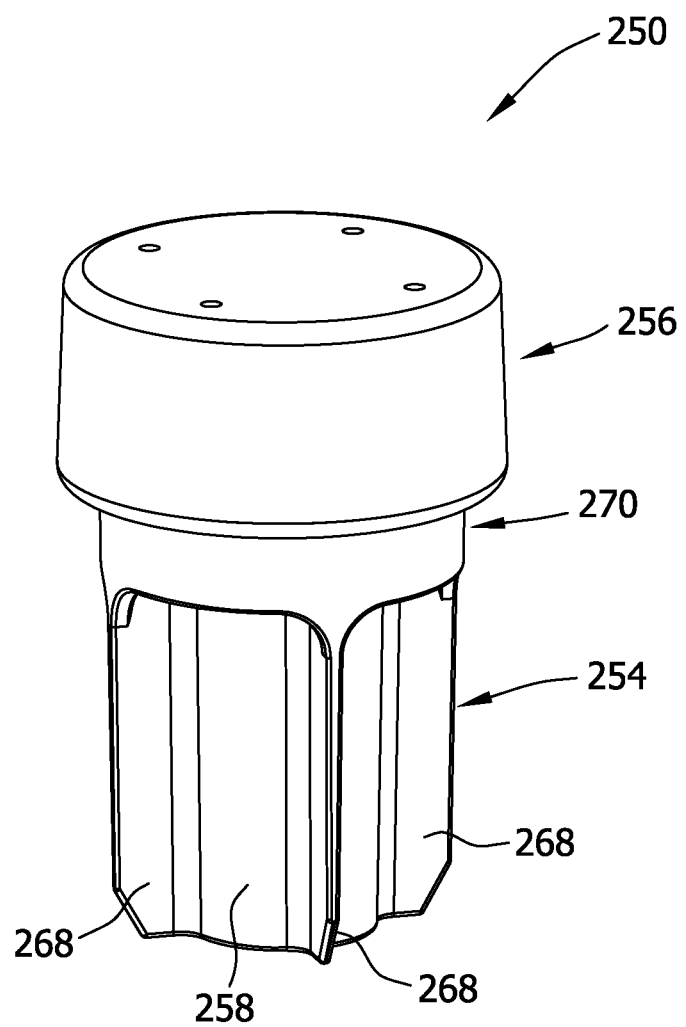
FIG. 34 is a perspective of the sterile vial holder in FIG. 18.
Figure 35:
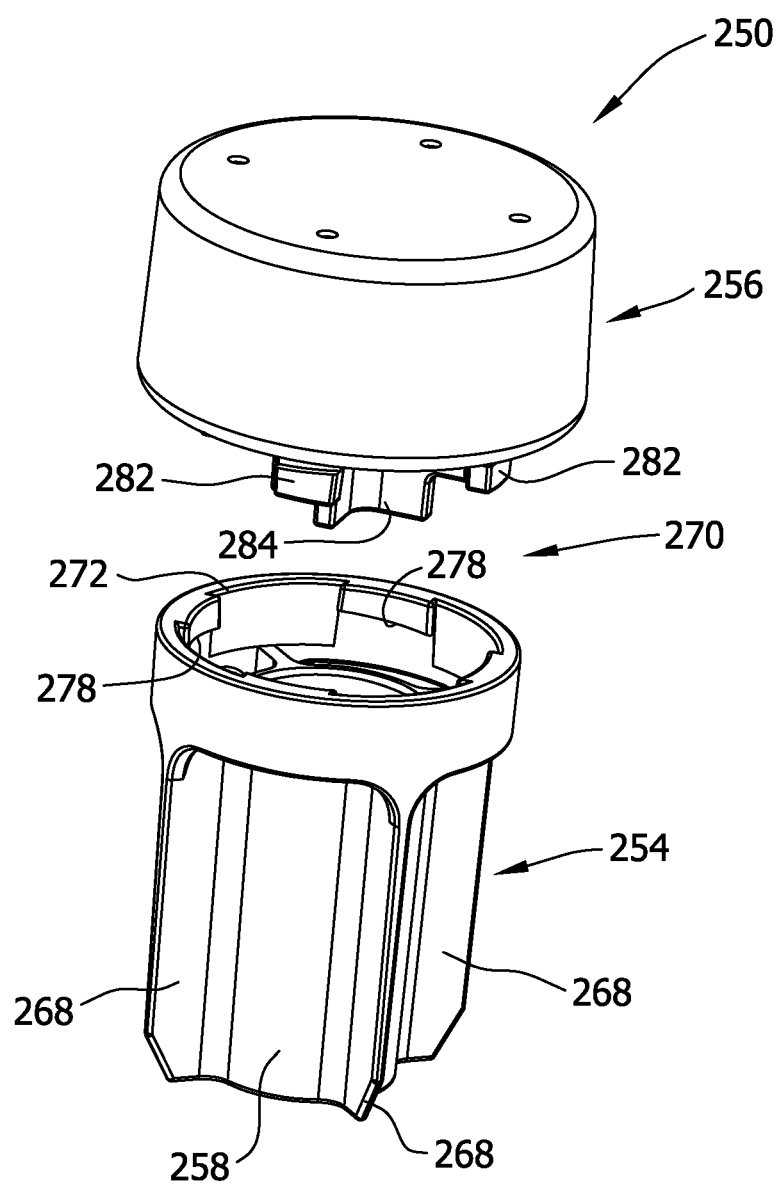
FIG. 35 is an exploded perspective of the sterile vial holder.

Referring to FIG. 23, as disclosed above the storage cap 162 is removably securable to the elution tool body 152 to configure the elution tool in the storage configuration. In the storage configuration, the storage cap 162 must be removed from the elution tool body 152 in order for a radiopharmacist or technician to withdraw a quantity of radiopharmaceutical from the elution vial 17. The storage cap 162 includes a storage cap body 232 (e.g., a generally cylindrical body) having a top 234 and a bottom 236, and a radiation shield 238 secured to the bottom of the storage cap body. The storage cap body 232 defines a socket 240 extending from the top 234 toward the bottom 236 of the storage cap body that is sized and shape for receiving the lower longitudinal portion 166 of the elution tool body 152. The socket 240 has an open top end to allow insertion of the lower longitudinal portion 166 of the elution tool body 152 into the socket. The radiation shield 238 is secured to the bottom 236 of the storage cap body 232 such that the shield is aligned and in opposing relationship with the access opening 174 in the elution tool body 152 when the storage cap 162 is removably secured to the elution tool 150. In the illustrated embodiment, the radiation shield 238 is a press insert into the storage cap body 232. The radiation shield 238 may be secured to the storage cap body 232 in other ways without departing from the scope of the present disclosure.

Referring to FIG. 23, the storage cap 162 is removably securable to the elution tool body 152 in substantially the same way as the dispensing cap 160, although the storage cap can be removably securable in other ways. More specifically, the storage cap 162 includes a plurality of magnetic couplers 244 secured to the storage cap body 232 and surrounding the socket 240. The magnetic couplers 244 are magnetically attracted to the annular coupler surface 216 of the elution tool body 152. It is understood that the elution tool body 152 may include magnetic couplers secured thereto, that are magnetically attracted to the magnetic couplers (or another component or structure) of the storage cap body. The dispensing cap 160 may be removably securable to the elution tool body 152 in other ways without departing from the scope of the present disclosure.

Figure 36:
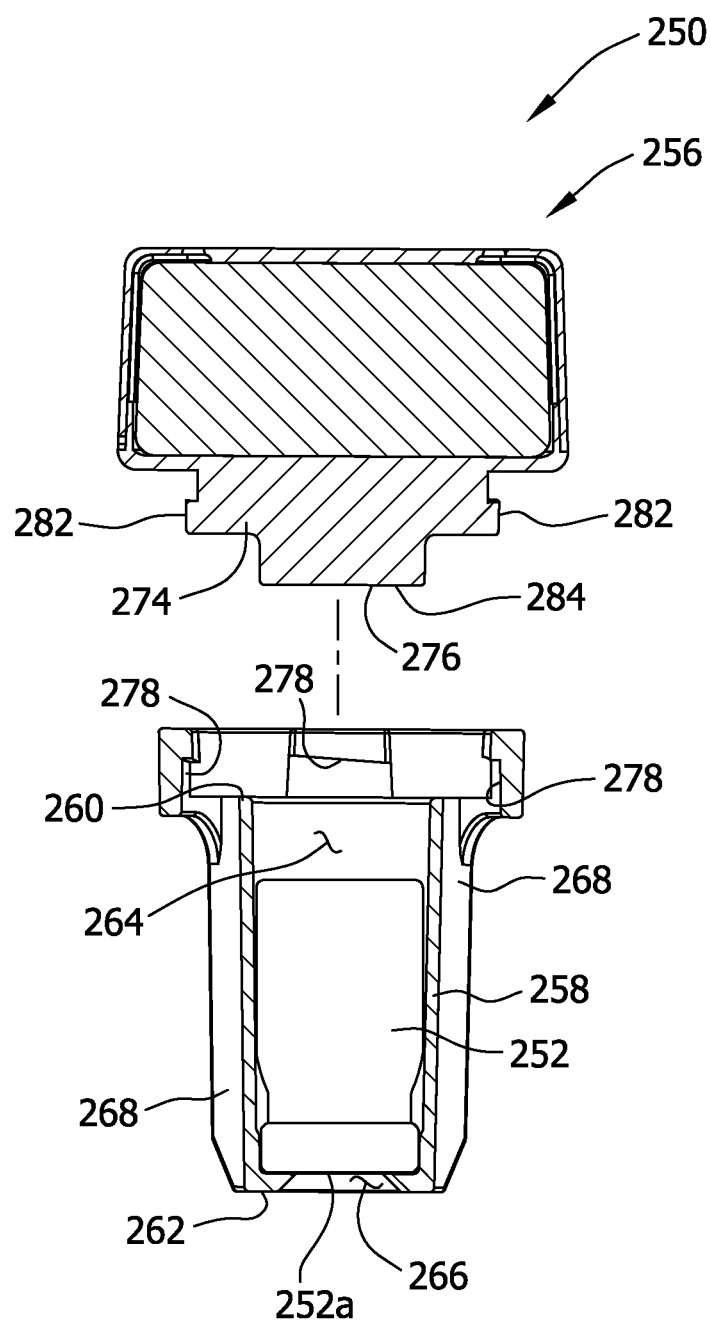
FIG. 36 is a sectional view of the exploded sterile vial holder.
Figure 37:
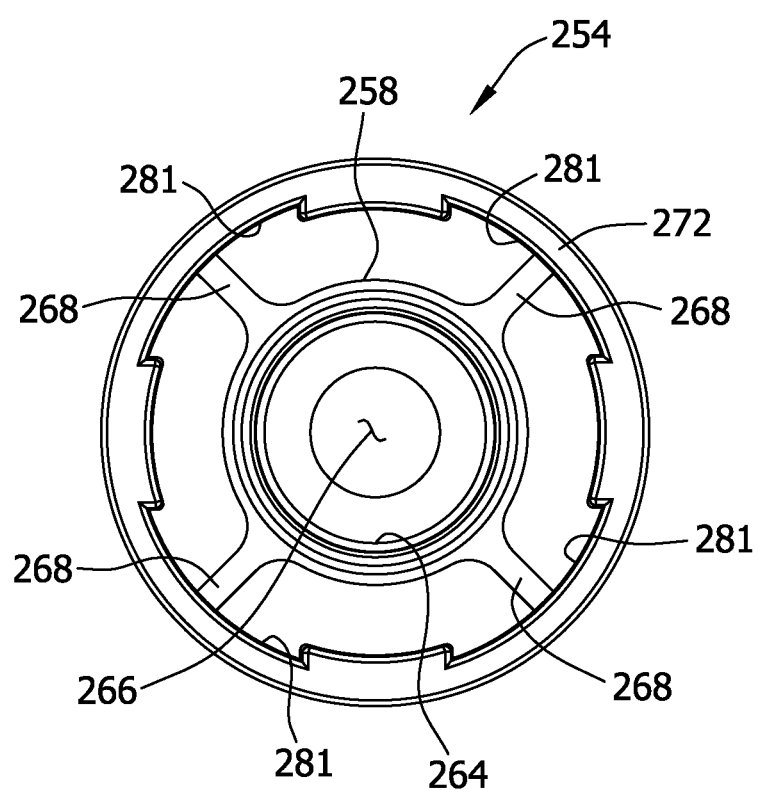
FIG. 37 is a top plan of a body of the sterile vial holder.

Referring to FIGS. 34-37, the radioisotope elution system 10 may also include a sterile vial holder, generally indicated at 250, for a vial 252 of sterile fluid (e.g., TechneStat™) in which the output needle 32 is stored when the elution system 10 is not in use. As explained in more detail below, after the elution process, the elution tool 150 may be withdrawn from the elution tool opening 79 in the auxiliary shield lid 24, at which time the sterile vial holder 250 can be inserted into the elution tool opening so that the output needle 32 pierces a septum 252a of the sterile fluid vial. The sterile vial holder 250 includes a body, generally indicated at 254, for holding the sterile vial 252 therein, and a cap, generally indicated at 256, that is removably securable to the body. The holder body 254 has a generally cylindrical receptacle 258 having an open top 260, a bottom 262, and a vial chamber 264 sized and shaped for receiving and retaining the sterile vial 252 therein. As shown in FIG. 36, the bottom 262 of the receptacle 258 defines an access opening 266 that is aligned with the septum 252a of the sterile vial 252 when the vial is received in the chamber 264 so that the output needle 32 pierces the septum and enters the sterile vial when the sterile vial holder 250 is inserted into the elution tool opening 79.

The holder body 254 includes a plurality of fins 268 (e.g., four fins) projecting radially outward from the receptacle 258 and spaced apart around the receptacle. The fins 268 define a diameter or cross-sectional dimension of the receptacle 258 that is sized and shaped to fit snugly within the elution tool opening 79 so that the access opening 266 (and the septum 252a) align with the output needle 32 when the holder 250 is inserted into the elution tool opening. The holder body 254 may be of other configurations without departing from the scope of the present disclosure.

The cap 256 of the sterile vial holder 250 is removably securable to the body 254 by a twist-lock mechanism, generally indicated at 270. The body 254 includes an annular female twist-lock component 272 that receives a male twist-lock component 274 projecting outward from a bottom surface 276 of the cap 256. The female twist-lock component 272 defines slots or grooves 278 that are spaced apart around an interior surface 280 of the female twist-lock component to define gaps 281. The male twist-lock component 274 includes a plurality of tabs 282 that are receivable in the gaps 281 defined between the grooves 278 of the female twist-lock component, and that enter the grooves 278 when the cap 256 is rotated about its longitudinal axis relative to the holder body 254. When the tabs 282 are received in the grooves 278, the twist-lock mechanism inhibits relative longitudinal movement between the cap 256 and the holder body 254. In the illustrated embodiment, the male twist-lock component 274 also includes a longitudinal projection 284 that enters the vial chamber 264 of the receptacle 258 and abuts the bottom of the sterile vial 252 to limit or restrict longitudinal movement of the sterile vial in the chamber. It is understood that the cap 256 may be releasably securable to the body 254 in other ways without departing from the scope of the present disclosure.

The holder body 254 may be a one-piece component formed (e.g., molded) from plastic or other material that has a density less than the density of material that provides suitable radiation shielding, such as that provided by lead, tungsten, tungsten impregnated plastic, depleted uranium. The cap 256, on the other hand, may include suitable radiation shielding material such as depleted uranium, tungsten, tungsten impregnated plastic, or lead. In one example, the cap may be formed by a two-step overmolding process. In such a process, a radiation shielding core—which may include a suitable radiation shielding material such as depleted uranium, tungsten, tungsten impregnated plastic, or lead—is provided. A first molded part is molded with a first thermoplastic material to form the top 260. Next, the core is placed into the first molded part. Finally, this assembly is overmolded with a second thermoplastic material to form the bottom 262, the male twist-lock component 274, and the longitudinal projection 284. The first and second thermoplastic materials, respectively, may include polypropylene and polycarbonate, or other material, and the first and second thermoplastic materials may be of the same material. Other methods of making the cap 256 may be used.

Figure 38:
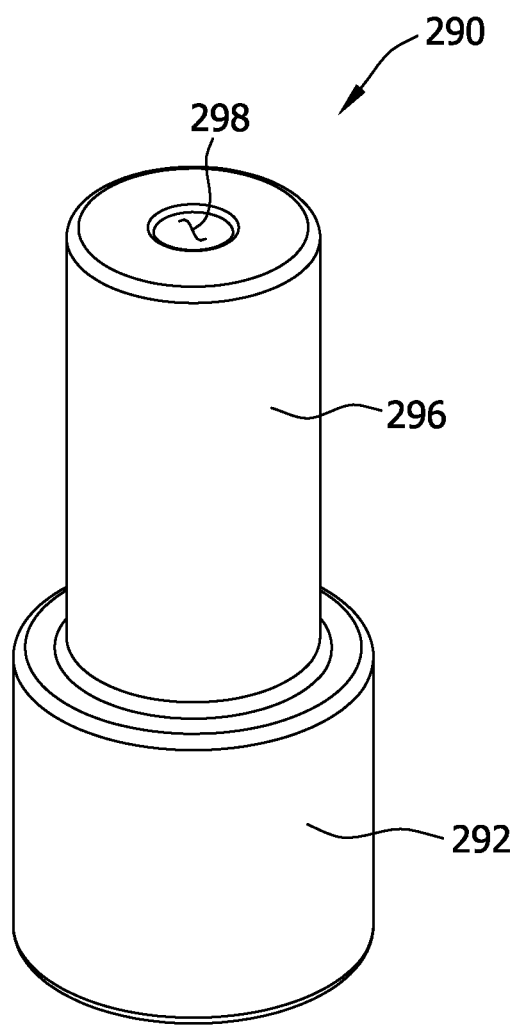
FIG. 38 is a perspective of a re-covering tool.
Figure 39:
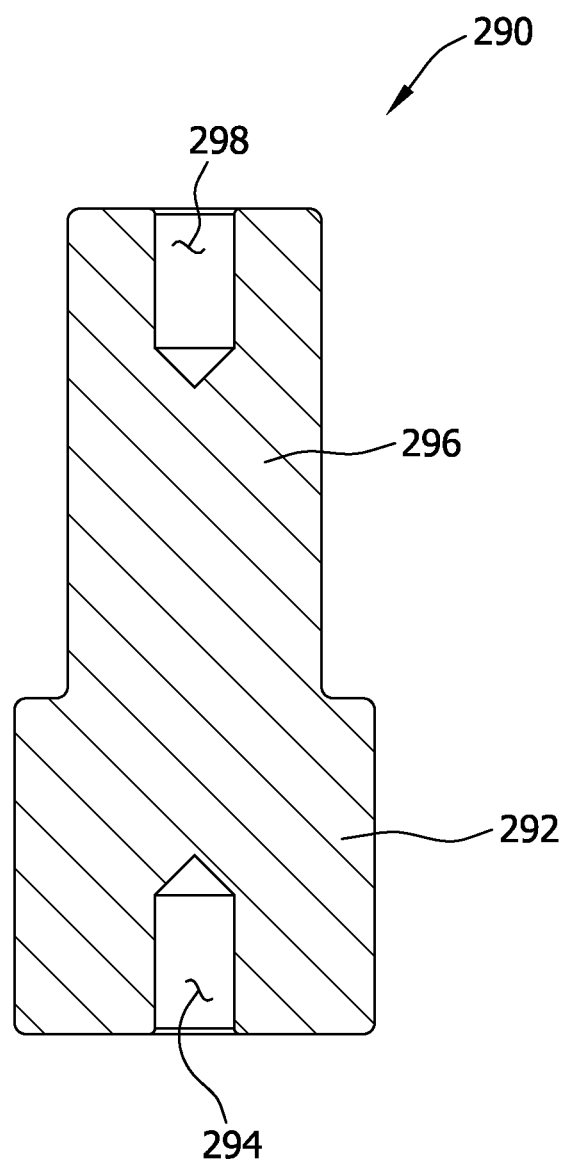
FIG. 39 is a sectional view of the re-covering tool.

Referring to FIGS. 38 and 39, the elution system 10 may also include a re-covering tool, generally indicated at 290, for reapplying the input/venting needle cover 55a and the output needle cover 55b on the respective input and venting needles 30, 54 and the output needle 32. The re-covering tool 290 has a first longitudinal portion 292, defining an output needle cover cavity 294 for snugly receiving the output needle cover 55b therein, and a second longitudinal portion 296, defining an input/venting needle cover cavity 298 for snugly receiving the input/venting needle cover 55a therein. The first longitudinal portion 292 has a size and shape such that it is snugly receivable in the elution tool opening 79 in the auxiliary shield lid 24, and the second longitudinal portion 296 has a size and shape such that it is snugly receivable in the eluant vial opening 80 in the auxiliary shield lid. The re-covering tool 290 may be formed from plastic, or other suitable material, and may be molded as a single, one-piece structure.

To reapply the covers 55a, 55b, the radiopharmacist or technician inserts the covers into the respective cavities 294, 298. The covers 55a, 55b are held in the respective cavities 294, 298 by friction-fit engagement between the walls of the cavities and the covers. The radiopharmacist or technician can then insert the second longitudinal portion 296 into the eluant vial opening 80, whereupon the input and venting needles 30, 54 pierce the cover 55a. Upon withdrawing the second longitudinal portion 296 from the eluant vial opening 80, the cover 55a remains secured to the input and venting needles 30, 54. The radiopharmacist or technician can then insert the first longitudinal portion 292 into the elution tool opening 79 to reapply the cover 55b in a similar manner. It is understood that the covers 55a, 55b may be reapplied in any order without departing from the scope of the present disclosure.

In a method of using the radioisotope elution system 10, the radiopharmacist or technician manually inserts the radioisotope generator 12 into the cavity 22 of the auxiliary shield body 20, the handle is folded down, and the cap cover 56 is removed in the manner set forth above. The auxiliary shield lid 24 is then manually placed in the cavity, on top of the radioisotope generator 12. The lid 24 may be rotated to thereby mate the male alignment structure 81 on the lid with the female alignment structure (i.e., the recessed portion 40 and the U-shaped channel 42) in the cap 38 of the generator 12. Upon mating, the eluant vial opening 80 is disposed over and generally vertically aligned with the input needle 30 and the venting needle 54, and elution tool opening 79 is disposed over and generally vertically aligned with the output needle 32. Using forceps (or another tool), the radiopharmacist or technician removes the two covers 55a and 55b. The eluant vial 17 is manually inserted into the passageway defined by the wings 100 and the eluant vial opening 80. The passageway guides the eluant vial 17 in a substantially vertical direction, such that the longitudinal axis of the eluant vial is generally aligned with the axes of the input needle 30 and the venting needle 54. More specifically, the passageway guides the eluant vial 17 such that the input needle 30 and the venting needle 54 pierce the septum of the vial to fluidly connect the interior of the eluant vial to the generator 12. The radiopharmacist or technician can view the bottom 116 of the eluant vial 18 through the notches 118 in the respective wings 100 when the vial is received in the passageway 107 to confirm that the eluant vial 18 is fully inserted onto the generator 12. Accordingly, the radiopharmacist or technician does not have to position his/her head directly above the lid 24 to confirm that the needles 30, 54 actually pierced the eluant vial septum. To this effect, the radiopharmacist or technician reduces any likelihood of radiation exposure from the generator 12 when positioning his/her head over the eluant vial opening 80. Once confirmation is made that the vial is properly placed, the eluant shield 136 may be placed over the bottom of the eluant vial in the manner set forth above.

In this method, the elution vial 17 is inserted into the elution tool 150 and the lid 158 is closed in the manner set forth above. The elution tool, which does not have either the dispensing cap 160 or the storage cap 162 secured thereto, is manually inserted into the elution tool opening 79 such that the output needle 32 pierces the septum of the elution vial to fluidly connect the elution vial to the generator 12. The vacuum (or reduced pressure) in the elution vial 17 draws the saline from the vial 18 through the radioisotope column and into the elution vial 17.

After the elution vial 17 is filled with the desired quantity of radioisotope-containing saline, the elution tool 150 can be manually removed from the lid 24, at which time the dispensing cap 160 or the storage cap 162 can be secured to the elution tool body 152 in the manner set forth above. With the dispensing cap 160 secured to the elution tool body 152, the radiopharmacist or technician can withdraw desired quantities of the radiopharmaceutical from the elution vial 17 in the manner set forth above.

With the elution tool 150 removed from the lid 24, the sterile vial holder 250 can be inserted into the elution tool opening 79 so that the output needle 32 pierces the sterile vial 252. The now empty eluant vial 18 may remain on the radioisotope generator 12 until a subsequent elution in order to keep the needles 30, 54 sterile. When it is time for a subsequent elution, the eluant vial 18 can be manually removed from lid 24, such as by the radiopharmacist or technician inserting his/her thumb and forefinger into the respective finger recesses 90 and then into the respective finger channels 112 to grip (or pinch) the eluant vial. The radiopharmacist or technician can then lift the eluant vial 18 upward off the needles 30 and 54 and out of the lid 24.

When introducing elements of the present invention or the embodiment(s) thereof, the articles "a", "an", the and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. A radiation shield for an eluant vial in combination with a radiation shielding lid for use with a radiopharmaceutical elution system, the radiation shield comprising:
   a shield body having a closed top, an open bottom, and defining a cavity extending from the bottom toward the top, wherein the cavity is designed to accommodate at least a bottom portion of an eluant vial; and
   a pair of shielding wings extending downward from the bottom and partially surrounding the cavity,
   wherein the shield body and the shielding wings comprise at least one of depleted uranium, tungsten, and tungsten impregnated plastic;
   the radiation shielding lid comprising a body having an upper surface and an opposing lower surface; a first opening defined in the body, the first opening having a lower end at the lower surface of the body and an upper end intermediate the upper and lower surfaces of the body; a pair of finger recesses defined in the body, the recesses having an upper end and a lower end, wherein at least portions of the upper ends of the recesses are located at the upper surface of the body, and wherein at least portions of the lower ends of the recesses are located at the upper end of the first opening; and first and second wings, each of which extends upward from the upper end of the first opening and only partially about a circumference of the upper end of the first opening such that gaps are defined between the first wing and the second wing.

2. The radiation shield set forth in claim 1, wherein the body comprises at least one of depleted uranium, tungsten, tungsten impregnated plastic, and lead.

3. The radiation shield set forth in claim 1, wherein the shielding wings of the radiation shield are receivable in the finger recesses such that the shielding wings are in opposing relationship with the gaps defined between the first and second wings of the lid and the top of the shield body covers the first and second wings.

4. The radiation shield set forth in claim 1, wherein the finger recesses of the radiation shielding lid have a generally ellipsoidal shape, and wherein each shielding wing of the radiation shield includes an exterior surface having a curved portion sized and shaped to engage the finger recesses of the radiation shielding lid.

5. The radiation shield set forth in claim 4, wherein each shielding wing further includes a flat bottom surface, wherein the bottom surface is substantially parallel to the bottom of the shield body.

6. The radiation shield set forth in claim 1, wherein the finger recesses are diametrically opposed to one another with respect to the first opening, and wherein the shielding wings are diametrically opposed to one another about the cavity in the shield body.

7. The radiation shield set forth in claim 1 wherein the radiation shielding lid further comprises a second opening defined in the body, the second opening having a lower end at the lower surface of the body and an upper end at the upper surface of the body, the second opening being spaced apart and separate from the first opening.

8. The radiation shield set forth in claim 1, wherein the shield body and the shielding wings further comprise at least one of polypropylene and polycarbonate.

9. The radiation shield set forth in claim 1, further comprising a radiation shielding core comprising at least one of depleted uranium, tungsten, tungsten impregnated plastic, and lead, wherein the shielding body and shielding wings are at least partially constructed from an overmolded thermoplastic material.

10. The radiation shield set forth in claim 1, wherein the cavity has a generally cylindrical shape, and the shielding wings extend circumferentially about the cavity.

11. A radiation shield for an eluant vial in combination with a radiation shielding lid for use with a radiopharmaceutical elution system, the radiation shield comprising:

a shield body having a closed top, an open bottom, and defining a cavity extending from the bottom toward the top, wherein the cavity is designed to accommodate at least a bottom portion of an eluant vial; and a pair of shielding wings extending downward from the bottom and partially surrounding the cavity, wherein the shield body and the shielding wings comprise at least one of depleted uranium, tungsten, and tungsten impregnated plastic;

the radiation shielding lid comprising a body having an upper surface and an opposing lower surface, wherein the body comprises at least one of depleted uranium, tungsten, tungsten impregnated plastic, and lead; a first opening defined in the body, the first opening having a lower end at the lower surface of the body and an upper end intermediate the upper and lower surfaces of the body; and a recess defined in the body, the recess having an upper end and a lower end, wherein at least a portion of the upper end of the recess is located at the upper surface of the body, and wherein at least a portion of the lower end of the recess is located at the upper end of the first opening; and first and second wings, each of which extends upward from the upper end of the first opening and only partially about a circumference of the upper end of the first opening such that gaps are defined between the first wing and the second wing.

12. The radiation shield set forth in claim 11, wherein the body comprises at least one of depleted uranium, tungsten, tungsten impregnated plastic, and lead.

13. The radiation shield set forth in claim 11, wherein the radiation shielding lid further comprises a second opening defined in the body, the second opening having a lower end at the lower surface of the body and an upper end at the upper surface of the body, the second opening being spaced apart and separate from the first opening.

* * * * *